United States Patent
Gray et al.

(10) Patent No.: US 10,870,636 B2
(45) Date of Patent: Dec. 22, 2020

(54) PYRIMIDINES AS EGFR INHIBITORS AND METHODS OF TREATING DISORDERS

(71) Applicant: Dana-Farber Cancer Institute, Inc., Boston, MA (US)

(72) Inventors: Nathanael S. Gray, Boston, MA (US); Pasi Janne, Needham, MA (US); Hwan Geun Choi, Daegu (KR); Jaebong Jang, Boston, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 16/290,153

(22) Filed: Mar. 1, 2019

(65) Prior Publication Data
US 2019/0194169 A1    Jun. 27, 2019

Related U.S. Application Data

(62) Division of application No. 15/536,486, filed as application No. PCT/US2015/000286 on Dec. 23, 2015, now Pat. No. 10,266,517.

(60) Provisional application No. 62/096,053, filed on Dec. 23, 2014.

(51) Int. Cl.
| | | |
|---|---|---|
| C07D 471/04 | (2006.01) | |
| A61P 35/00 | (2006.01) | |
| C07D 403/04 | (2006.01) | |
| C07D 403/14 | (2006.01) | |
| C07D 487/04 | (2006.01) | |

(52) U.S. Cl.
CPC ......... *C07D 403/04* (2013.01); *C07D 403/14* (2013.01); *C07D 471/04* (2013.01); *C07D 487/04* (2013.01)

(58) Field of Classification Search
CPC combination set(s) only.
See application file for complete search history.

(56) References Cited

U.S. PATENT DOCUMENTS

| | | |
|---|---|---|
| 2013/0053409 A1 | 2/2013 | Butterworth et al. |
| 2013/0072469 A1 | 3/2013 | Singh et al. |
| 2017/0008889 A1 | 1/2017 | Lan et al. |
| 2017/0313714 A1 | 11/2017 | Wei et al. |
| 2017/0355696 A1 | 12/2017 | Jiang |

FOREIGN PATENT DOCUMENTS

| | | |
|---|---|---|
| WO | WO-2009064835 A1 | 5/2009 |
| WO | WO-2010129053 A2 | 11/2010 |
| WO | WO-2013014448 A1 | 1/2013 |
| WO | WO-2015127872 A1 | 9/2015 |
| WO | WO-2015188777 A1 | 12/2015 |
| WO | WO-2016054987 A1 | 4/2016 |
| WO | WO-2016070816 A1 | 5/2016 |
| WO | WO 2018/115218 A1 | 6/2018 |
| WO | WO 2018/220149 A1 | 6/2018 |

OTHER PUBLICATIONS

Galvani et al. Current Pharmaceutical Design vol. 19, 818-832. (Year: 2013).*
Choo et al. Targeted Oncology (2018) 13:141-156 (Year: 2018).*
Thomas et al. Frontiers in Oncology vol. 9, p. 1-16 (Year: 2019).*
Artega, C. L. "The Epidermal Growth Factor Receptor: From Mutant Oncogene in Nonhuman Cancers to Therapeutic Target in Human Neoplasia", J. Clin. Oncol., 2001, vol. 19, p. 32-40.
Banker et al. (1996) "Modern Pharmaceutics", 3rd Ed. p. 596.
Burger's Medicinal Chemistry, (1995) edited by Manfred E.Wolff, 5th Ed. Part 1, pp. 975-977.
Cross, D.A. et al. "AZD9291, an Irreversible EGFR TM, Overcomes T790M-Mediated Resistance to EGFR Inhibitors in Lung Cancer", Cancer Discov. 2014, p. 1046-1061.
Li, D. et al. "BIBW2992, an irreversible EGFR/HER2 inhibitor highly effective in preclinical lung cancer models", Oncogene, 2008, vol. 27, p. 4702-4711.
Lynch, T. J. et al. "Activating Mutations in the Epidermal Growth Factor Receptor Underlying Responsiveness of Non-Small-Cell Lung Cancer to Gefitinib", The New England Journal of Medicine, 2004, vol. 350, No. 21, p. 2129-2139.
Machine Translation for CN application 201410534203.9 filed Oct. 11, 2014 (for WO2016/054987).
Maemondo, M. et al. "Gefitinib or Chemotherapy for Non-Small-Cell Lung Cancer with Mutated EGFR", The New England Journal of Medicine, 2010, 362, p. 2380-2388.
Miller V.A. et al. "Afatinib versus placebo for patients with advanced, metastatic non-small-cell lung cancer after failure of erlotinib, gefitinib, or both, and one or two lines of chemotherapy (LUX-Lung 1): a phase 2b/3 randomised trial", Lancet Oncol., 2012, vol. 13, p. 528-538.
Mitsudomi T. et al. "Gefitinib versus cisplatin plus docetaxel in patients with non-small-cell lung cancer harbouring mutations of the epidermal growth factor receptor (WJTOG3405): an open label, randomised phase 3 trial", Lancet Oncol., 2010, vol. 11, p. 121-128.
Mok, T.S. et al. "Gefitinib or Carboplatin-Paclitaxel in Pulmonary Adenocarcinoma", The New England Journal of Medicine, 2009, vol. 361, No. 10, p. 947-957.

(Continued)

*Primary Examiner* — Emily A Bernhardt
(74) *Attorney, Agent, or Firm* — Lathrop GPM, LLP; Brian C. Trinque

(57) ABSTRACT

The application relates to a compound having Formula (I):

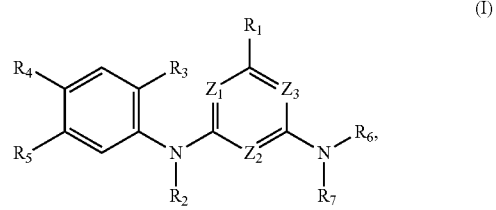

which modulates the activity of EGFR, a pharmaceutical composition comprising the compound, and a method of treating or preventing a disease in which EGFR plays a role.

18 Claims, 2 Drawing Sheets

(56) References Cited

OTHER PUBLICATIONS

Paez J.G. et al. "EGFR Mutations in Lung Cancer: Correlation with Clinical Response to Gefitinib Therapy", Science, 2004, vol. 304, p. 1497-1500.
Priority document for WO 2015/127872 filed Feb. 25, 2014.
Priority document for WO 2016/054987 filed Oct. 11, 2014.
Priority document for WO 2016/070816 filed Nov. 5, 2014.
Raymond E. et al. "Epidermal Growth Factor Receptor Tyrosine Kinase as a Target for Anticancer Therapy", Drugs 2000, vol. 60, Suppl. 1, p. 15-23.
Rivkin, A. et al. "Piperazinyl pyrimidine derivatives as potent γ-secretase modulators", Bioorganic & Medicinal Chemistry Letters, 2010, vol. 20, No. 3, p. 1269-1271.
Rosell R. et al. "Erlotinib versus standard chemotherapy as first-line treatment for European patients with advanced EGFR mutation-positive non-small-cell lung cancer (EURTAC): a multicentre, open-label, randomised phase 3 trial", Lancet Oncol., 2012, vol. 13, p. 239-246.
Salomon et al. "Epidermal growth factor-related peptides and their receptors in human malignancies", Critical Reviews in Oncology/Hematology, 1995, vol. 19, p. 183-232.
Sequist L.V. et al. "Phase III Study of Afatinib or Cisplatin Plus Pemetrexed in Patients with Metastatic Lung Adenocarcinoma with EGFR Mutations", Journal of Clinical Onoclogy, 2013, vol. 31, p. 3327-3334.
Seymour L. K., "Epidermal Growth Factor Receptor as a Target: Recent Developments in the Search for Effective New Anti-Cancer Agents", Current Drug Targets, 2001, vol. 2, p. 117-133.
Voldborg et al. "Epidermal growth factor receptor (EGFR) and EGRF mutations, function and possible role in clinical trials", Annals of Oncology, 1997, vol. 8, p. 1197-1206.
Walter A.O. et al. "Discovery of a Mutant-Selective Covalent Inhibitor of EGFR that Overcomes T790M Mediated Resistance in NSCLC", Cancer Discovery, 2013, vol. 3, p. 1404-1415.
Ward, R. A. et al. "Structure- and Reactivity-Based Development of Covalent Inhibitors of the Activating and Gatekeeper Mutant Forms of the Epidermal Growth Factor Receptor (EGFR)", Journal of Medicinal Chemistry, 2013, vol. 56, p. 7025-7048.
Wu, Y.L. et al. "Afatinib versus cisplatin plus gemcitabine for first-line treatment of Asian patients with advanced non-small-cell lung cancer harbouring EGFR mutations (LUX-Lung 6): an open-label, randomised phase 3 trial", Lancet Oncology, 2014, vol. 14, p. 213-222.
Yu, H.A. et al. "Analysis of Tumor Specimens at the Time of Acquired Resistance to EGFR-TKI Therapy in 155 Patients with EGFR-Mutant Lung Cancers", Clinical Cancer Research, 2013, vol. 19, p. 2240-2247.
Yun C.H. et al. "The T790M mutation in EGFR kinase causes drug resistance by increasing the affinity for ATP", Proc. Natl. Acad. Sci., USA 2008, vol. 105, No. 6, p. 2070-2075.
Zhou, C. et al. "Erlotinib versus chemotherapy as first-line treatment for patients with advanced EGFR mutation-positive non-small-cell lung cancer (OPTIMAL, CTONG-0802): a multicentre, open-label, randomised, phase 3 study", Lancet Oncology, 2011, vol. 12, p. 735-742.
Zhou, W. et al. "Novel mutant-selective EGFR kinase inhibitors against EGFR T790M" Nature, 2009, vol. 462, p. 1070-1074.

\* cited by examiner

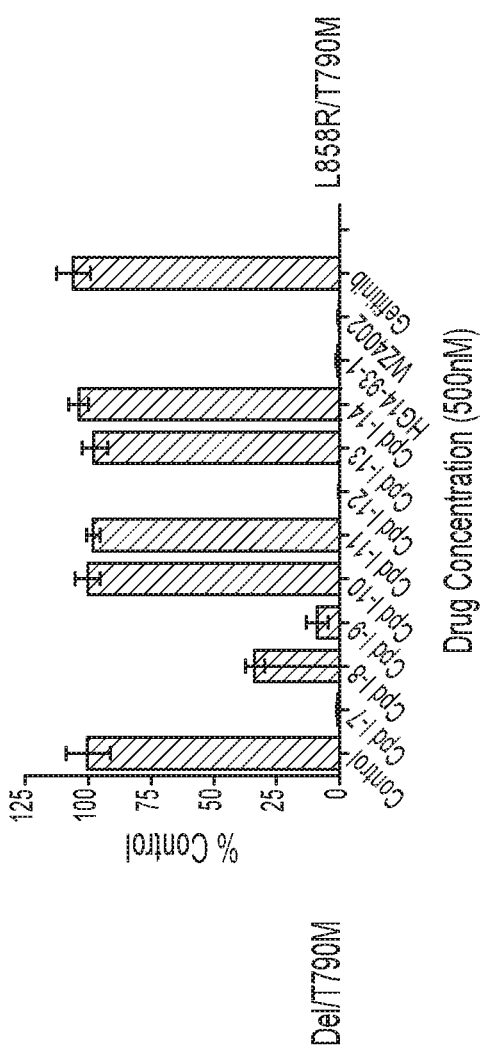
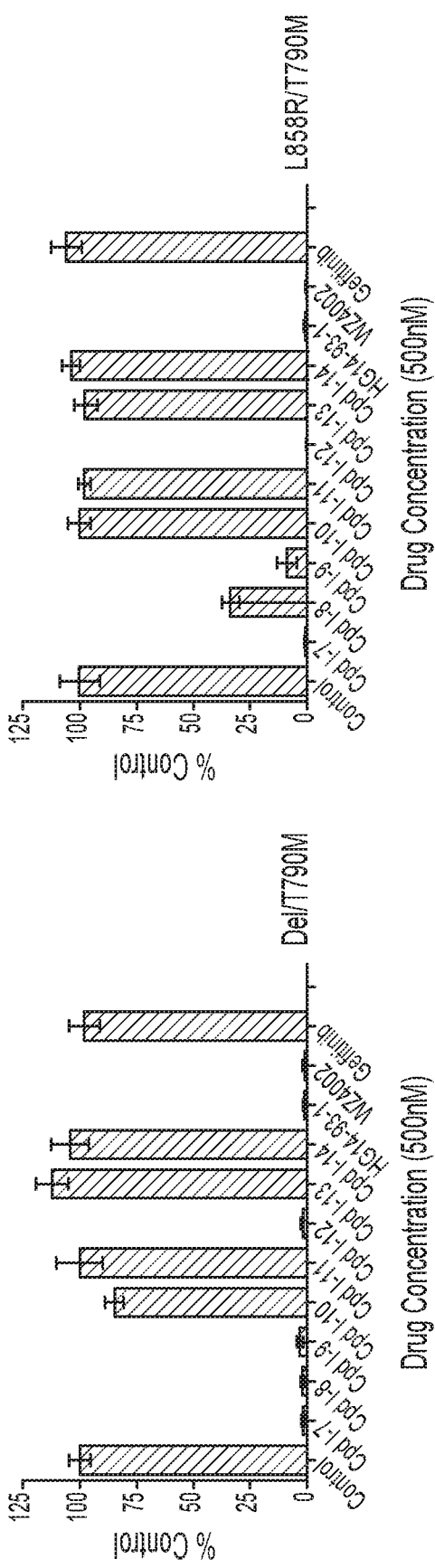
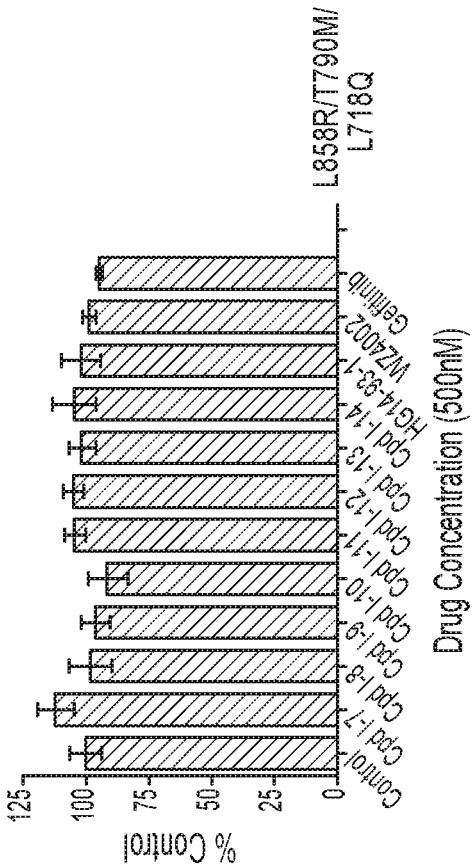
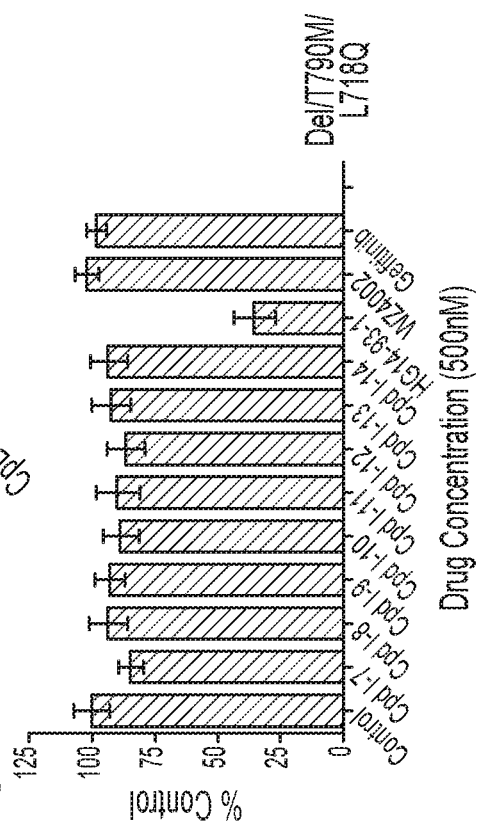
Figure 2A
Figure 2B
Figure 2C
Figure 2D

PYRIMIDINES AS EGFR INHIBITORS AND METHODS OF TREATING DISORDERS

CROSS-REFERENCE TO RELATED APPLICATIONS

This application is a division of U.S. Ser. No. 15/536,486 (now allowed), filed on Jun. 15, 2017, which is a U.S. National Phase application, filed under 35 U.S.C. § 371, of International No. PCT/US2015/000286, filed on Dec. 23, 2015, which claims priority to, and the benefit of, U.S. Provisional Application No. 62/096,053, filed on Dec. 23, 2014, the contents of each of which are incorporated herein by reference in their entireties.

STATEMENT AS TO FEDERALLY SPONSORED RESEARCH

This invention was made with government support under grant number CA154303 awarded by The National Institutes of Health. The government has certain rights in the invention.

BACKGROUND

The epidermal growth factor receptor (EGFR, Erb-B1) belongs to a family of proteins, involved in the proliferation of normal and malignant cells (Artega, C. L., J. Clin. Oncol. 19, 2001, 32-40). Overexpression of Epidermal Growth Factor Receptor (EGFR) is present in at least 70% of human cancers (Seymour, L. K., Curt. Drug Targets 2, 2001, 117-133) such as, non-small cell lung carcinomas (NSCLC), breast cancers, gliomas, squamous cell carcinoma of the head and neck, and prostate cancer (Raymond et al., Drugs 60 Suppl. 1, 2000, discussion 41-2; Salomon et al., Crit. Rev. Oneal. Hematol. 19, 1995, 183-232; Voldborg et al., Ann. Oneal. 8, 1997, 1197-1206). The EGFR-TK is therefore widely recognized as an attractive target for the design and development of compounds that can specifically bind and inhibit the tyrosine kinase activity and its signal transduction pathway in cancer cells, and thus can serve as either diagnostic or therapeutic agents. For example, the EGFR tyrosine kinase (EGFR-TK) reversible inhibitor, TARCEVA®, is approved by the FDA for treatment of NSCLC and advanced pancreatic cancer. Other anti-EGFR targeted molecules have also been approved including LAPATINIB® and IRESSA®. Epidermal growth factor receptor (EGFR) tyrosine kinase inhibitors (TKIs) are effective clinical therapies for EGFR mutant advanced non small cell lung cancer (NSCLC) patients (Mok, T. S., et al., N. Engl. J. Med. 361, 2009, 947-57; Paez, J. G., et al., Science. 304, 2004, 1497-500; Lynch, T. J., et al., N. Engl. J. Med. 350, 2004, 2129-39; Rosell, R., et al., Lancet Oncol. 13, 2012, 239-46). Several randomized clinical trials have demonstrated that EGFR TKIs are more effective, as measured by response rate (RR) and progression free survival (PFS), than chemotherapy when used as initial systemic treatment for advanced EGFR mutant NSCLC (Mok, T. S., et al., N. Engl. J. Med. 361, 2009, 947-57; Rosell, R., et al., Lancet Oncol. 13, 2012, 239-46; Sequist, L. V. et al., J. Clin. Oncol. 31, 2013, 3327-34; Wu, Y. L., et al., Lancet Oncol. 15, 2014, 213-22; Maemondo, M., et al. N. Engl. J. Med. 362, 2010, 2380-8; Zhou, C., et al., Lancet Oncol. 12, 2011, 735-42; Mitsudomi, T., et al., Lancet Oncol. 11, 2010, 121-8). However, the vast majority of patients will develop disease progression following successful treatment with an EGFR TKI. The most common mechanism of acquired resistance, detected in 60% of patients, is a secondary mutation in EGFR at position T790 (T790M) (Yu, H. A., et al., Clin. Cancer Res. 19, 2013, 2240-7). This mutation, leads to an increase in ATP affinity, thus making it more difficult for reversible EGFR TKIs gefitinib and erlotinib to bind the EGFR TKI domain (Yun C. H., et al., Proc. Natl. Acad. Sci. USA. 105, 2008, 2070-5).

Covalent EGFR inhibitors have emerged as strategies to inhibit EGFR T790M containing cancers. In preclinical models, afatinib, a covalent quinazoline based EGFR inhibitor, is effective both in models harboring only an EGFR activating mutation and in those with a concomitant T790M resistance mutation (Li, D., et al., Oncogene. 27, 2008, 4702-11). However, in lung cancer patients, afatinib is only effective in EGFR TKI naive EGFR mutant cancers and has a RR of <10% in patients with NSCLC that have developed resistance to gefitinib or erlotinib (Miller V. A., et al., Lancet Oncol. 13, 2012, 528-38). Afatinib is a potent inhibitor of both mutant and wild type (WT) EGFR. Inhibition of WT EGFR leads to toxicities, including skin rash and diarrhea, which limits the ability to escalate afatinib doses in patients to those necessary to inhibit EGFR T790M. Irreversible pyrimidine EGFR inhibitors, including the tool compound WZ4002 and clinical compounds CO-1686 and AZD9291, overcome many of the limitations of afatinib (Zhou, W., et al., Nature 462, 2009, 1070-4; Walter, A. O., et al., Cancer Discov. 3, 2013, 1404-15; Cross, D. A., et al., Cancer Discov. 2014). They are not only more potent on EGFR T790M, but also selectively inhibit mutant over WT EGFR and hence should lead to increased clinical efficacy and less toxicity compared with afatinib (Zhou, W., et al.; Walter, A. O., et al; Cross, D. A., et al.).

Despite the clinical efficacy of irreversible pyrimidine EGFR inhibitors, it is fully anticipated that patients will ultimately develop acquired resistance to these agents. To date little is known about the mechanisms of acquired resistance and whether cross resistance will occur to all irreversible pyrimidine based and to existing EGFR inhibitors. For these reasons, there remains a need for novel and potent small molecule irreversible pyrimidine EGFR inhibitors.

SUMMARY

The present application relates to compounds of Formula (I), as defined herein, that are capable of modulating EGFR activity. The application features methods of treating or preventing a disease in which EGFR plays a role in a subject in need thereof by administering to the subject a therapeutically effective amount of a compound of Formula (I), or a pharmaceutically acceptable salt, hydrate, solvate, prodrug, stereoisomer, or tautomer thereof, as defined herein. The methods of the application can be used to treat diseases in which EGFR plays a role by inhibiting the kinase activity of EGFR.

A first aspect of the application relates to compounds of Formula (I):

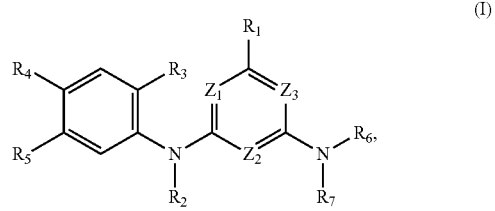

or pharmaceutically acceptable salts, hydrates, solvates, prodrugs, stereoisomers, or tautomers thereof, wherein $R_1$, $R_2$, $R_3$, $R_4$, $R_5$, $R_6$, $R_7$, $Z_1$, $Z_2$, and $Z_3$ are described herein in detail below.

Another aspect of the present application relates to a pharmaceutical composition comprising, a compound of Formula (I), or a pharmaceutically acceptable salt, hydrate, solvate, prodrug, stereoisomer, or tautomer thereof, and a pharmaceutically acceptable carrier.

Another aspect of the present application relates to a method of inhibiting a kinase. The method comprises administering to a subject in need thereof an effective amount of a compound of Formula (I), or a pharmaceutically acceptable salt, hydrate, solvate, prodrug, stereoisomer, or tautomer thereof.

In another aspect, the present application relates to a method of inhibiting epidermal growth factor receptor (EGFR). The method comprises administering to a subject in need thereof an effective amount of a compound of Formula (I), or a pharmaceutically acceptable salt, hydrate, solvate, prodrug, stereoisomer, or tautomer thereof.

Another aspect of the present application relates to a method of treating or preventing a disease. The method comprises administering to a subject in need thereof an effective amount of a compound of Formula (I), or a pharmaceutically acceptable salt, hydrate, solvate, prodrug, stereoisomer, or tautomer thereof.

In another aspect, the present application relates to a method of treating or preventing a kinase mediated disorder. The method comprises administering to a subject in need thereof an effective amount of a compound of Formula (I), or a pharmaceutically acceptable salt, hydrate, solvate, prodrug, stereoisomer, or tautomer thereof.

Another aspect of the present application relates to a method of treating or preventing a disease, wherein the disease is resistant to an EGFR targeted therapy, such as a therapy with gefitinib or erlotinib. The method comprises administering to a subject in need thereof an effective amount of a compound of Formula (I), or a pharmaceutically acceptable salt, hydrate, solvate, prodrug, stereoisomer, or tautomer thereof.

In another aspect, the present application relates to a method of treating or preventing cancer, wherein the cancer cell comprises an activated EGFR. The method comprises administering to a subject in need thereof an effective amount of a compound of Formula (I), or a pharmaceutically acceptable salt, hydrate, solvate, prodrug, stereoisomer, or tautomer thereof.

Another aspect of the present application relates to a method of treating or preventing cancer in a subject, wherein the subject is identified as being in need of EGFR inhibition for the treatment or prevention of cancer. The method comprises administering to the subject an effective amount of a compound of Formula (I), or a pharmaceutically acceptable salt, hydrate, solvate, prodrug, stereoisomer, or tautomer thereof.

In another aspect, the present application relates to a method of treating or preventing cancer, wherein the cancer cell comprises an activated ERBB2. The method comprises administering to a subject in need thereof an effective amount of a compound of Formula (I), or a pharmaceutically acceptable salt, hydrate, solvate, prodrug, stereoisomer, or tautomer thereof.

Another aspect of the present application relates to a method of treating or preventing cancer in a subject, wherein the subject is identified as being in need of ERBB2 inhibition for the treatment of cancer. The method comprises administering to the subject an effective amount of a compound of Formula (I), or a pharmaceutically acceptable salt, hydrate, solvate, prodrug, stereoisomer, or tautomer thereof.

Another aspect of the present application relates to a kit comprising a compound capable of inhibiting EGFR activity selected from a compound of Formula (I), or a pharmaceutically acceptable salt, hydrate, solvate, prodrug, stereoisomer, or tautomer thereof.

In another aspect, the present application relates to a compound of Formula (I), or a pharmaceutically acceptable salt, hydrate, solvate, prodrug, stereoisomer, or tautomer thereof, for use in the manufacture of a medicament for treating or preventing a disease associated in which EGFR plays a role.

Another aspect of the present application relates to the use of a compound of Formula (I), or a pharmaceutically acceptable salt, hydrate, solvate, prodrug, stereoisomer, or tautomer thereof, in the treatment or prevention of a disease in which EGFR plays a role.

The present application provides inhibitors of EGFR, such as EGFR containing one or more mutations, that are therapeutic agents in the treatment or prevention of diseases such as cancer and metastasis.

The present application further provides compounds and compositions with an improved efficacy and/or safety profile relative to known EGFR inhibitors. The present application also provides agents with novel mechanisms of action toward EGFR kinases in the treatment of various types of diseases including cancer and metastasis.

The details of the application are set forth in the accompanying description below. Although methods and materials similar or equivalent to those described herein can be used in the practice or testing of the present application, illustrative methods and materials are now described. Other features, objects, and advantages of the application will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this application belongs. All patents and publications cited in this specification are incorporated herein by reference in their entireties.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

BRIEF DESCRIPTION OF THE DRAWINGS

FIG. 2A is a bar graph showing the percentage of EGFR activity in an EGFR Del/T790M cell line when treated with various compounds of Formula (I) as compared to a control or samples treated with gefitinib or WZ4002.

FIG. 2B is a bar graph showing the percentage of EGFR activity in an EGFR L858R/T790M cell line when treated with various compounds of Formula (I) as compared to a control or samples treated with gefitinib or WZ4002.

FIG. 2C is a bar graph showing the percentage of EGFR activity in an EGFR Del/T790M/L718Q cell line when treated with various compounds of Formula (I) as compared to a control or samples treated with gefitinib or WZ4002.

FIG. 2D is a bar graph showing the percentage of EGFR activity in an EGFR L858R/T790M/L718Q cell line when treated with various compounds of Formula (I) as compared to a control or samples treated with gefitinib or WZ4002.

DETAILED DESCRIPTION

Compounds of the Application

Figure 1A:
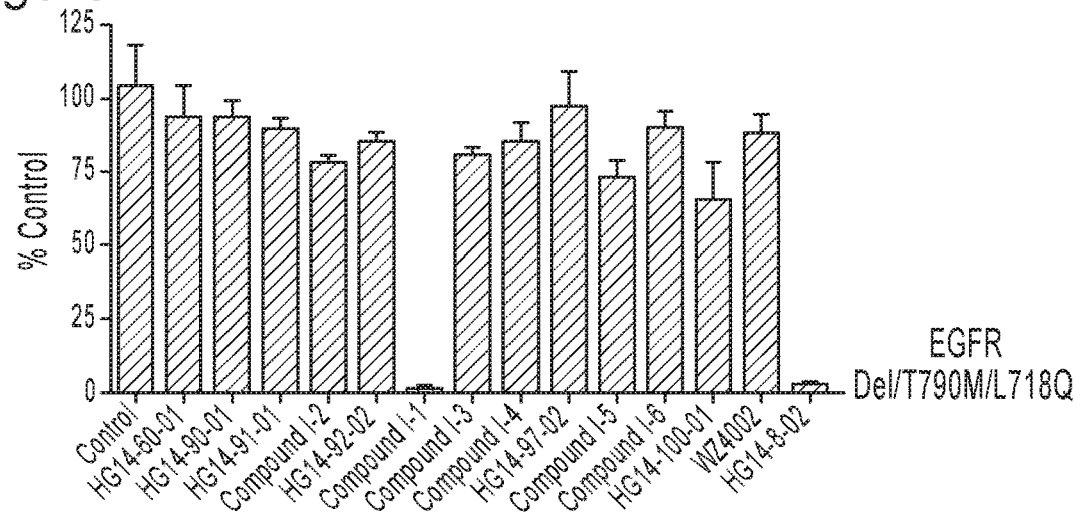
FIG. 1A is a bar graph showing the percentage of EGFR activity in an EGFR Del/T790M/L718Q cell line when treated with various compounds of Formula (I) as compared to a control or samples treated with WZ4002.
Figure 1B:
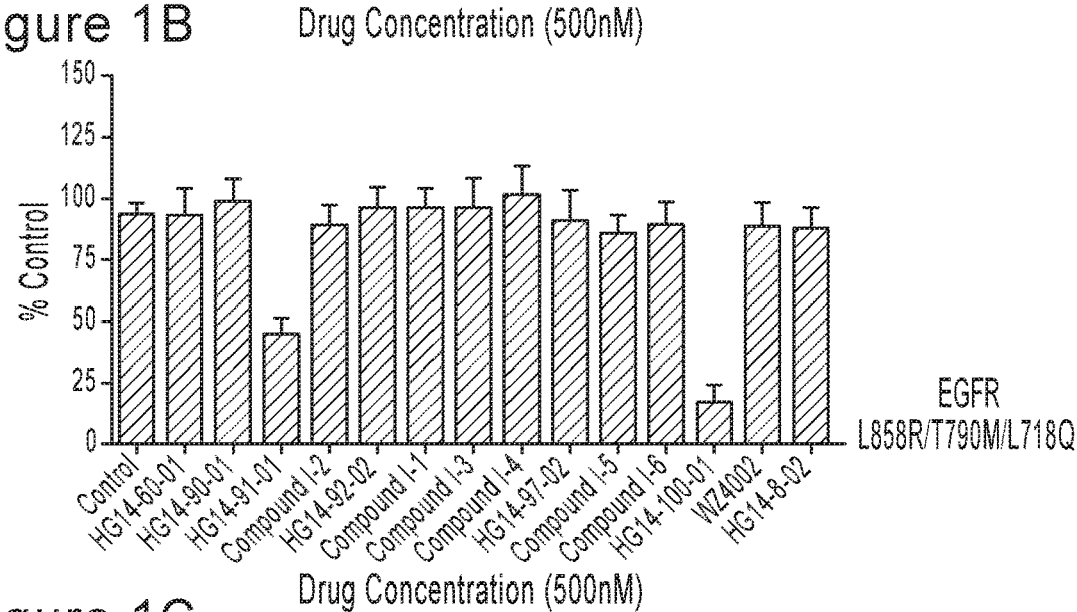
FIG. 1B is a bar graph showing the percentage of EGFR activity in an EGFR L858R/T790M/L718Q cell line when treated with various compounds of Formula (I) as compared to a control or samples treated with WZ4002.
Figure 1C:
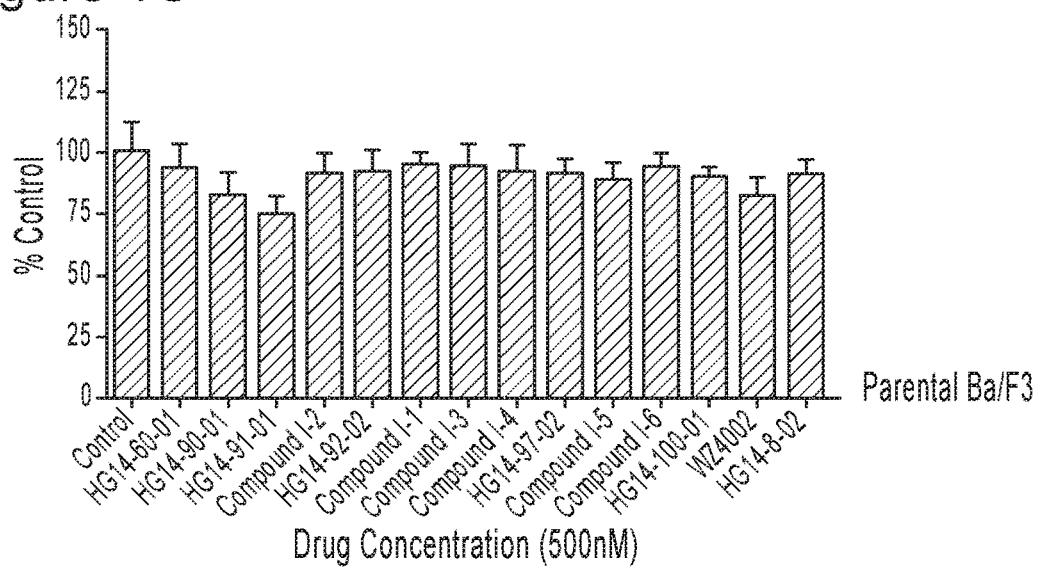
FIG. 1C is a bar graph showing the percentage of EGFR activity in an EGFR Parental BA/F3 cell line when treated with various compounds of Formula (I) as compared to a control or samples treated with WZ4002.

A first aspect of the application relates to compounds of Formula (I):

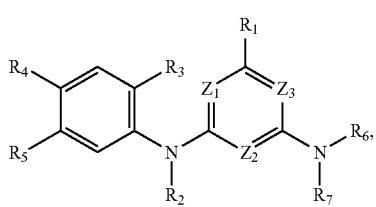

(I)

or pharmaceutically acceptable salts, hydrates, solvates, prodrugs, stereoisomers, or tautomers thereof, wherein:

$Z_1$, $Z_2$, and $Z_3$ are each independently N or $CR_8$, wherein at least two of $Z_1$, $Z_2$, and $Z_3$ are N;

$R_8$ is H, $(C_1-C_4)$ alkyl, $(C_1-C_4)$ haloalkyl, or halogen;

$R_1$ is H, $(C_1-C_4)$ alkyl, $(C_1-C_4)$ haloalkyl, $NH_2$, $NH(C_1-C_4)$ alkyl, $N((C_1-C_4)$ alkyl$)_2$, or halogen;

$R_2$ is H or $(C_1-C_6)$ alkyl;

$R_3$ is $(C_1-C_4)$ alkoxy, $(C_1-C_4)$ alkyl, $(C_1-C_4)$ haloalkyl, or halogen;

$R_4$ is $NR_9R_{10}$ or a 5- to 7-membered heterocycle comprising 1-3 heteroatoms selected from N, O, and S and optionally substituted with one or more $R_{11}$;

$R_9$ is H or $(C_1-C_4)$ alkyl;

$R_{10}$ is $(C_1-C_4)$ alkyl, $(C_1-C_4)$ alkyl-$NH(C_1-C_4)$ alkyl, or $(C_1-C_4)$ alkyl-$N((C_1-C_4)$ alkyl$)_2$;

or $R_9$ and $R_{10}$ together with the nitrogen atom to which they are attached form a 5- to 7-membered heterocycle optionally comprising 1 or 2 additional heteroatoms selected from N, O, and S and optionally substituted with one or more $R_{11}$;

each $R_{11}$ is independently $(C_1-C_4)$ alkyl, $(C_1-C_4)$ haloalkyl, $(C_1-C_4)$ alkoxy, or halogen;

$R_5$ is $NR_{12}C(O)R_{13}$ or $C(O)NR_{12}R_{13}$;

$R_{12}$ is H or $(C_1-C_6)$ alkyl;

$R_{13}$ is $(C_1-C_6)$ alkyl or $(C_2-C_6)$ alkenyl, wherein the alkyl or alkenyl is optionally substituted with one or more substituents independently selected from halogen, OH, CN, and $NH_2$;

$R_6$ and $R_7$ together with the nitrogen atom to which they are attached form a 5- or 6-membered heterocyclic or heteroaryl ring optionally comprising 1 or 2 additional heteroatoms selected from N, O, and S and optionally substituted with one or more $R_{14}$;

each $R_{14}$ is independently $(C_1-C_6)$ alkyl, $(C_1-C_6)$ haloalkyl, $(C_1-C_6)$ alkoxy, OH, $NH_2$, $NH(C_1-C_6)$ alkyl, $N((C_1-C_6)$ alkyl$)_2$, or halogen, or two $R_{14}$ present on adjacent atoms together with the atoms to which they are attached form a phenyl ring or a 5- or 6-membered heterocyclic or heteroaryl ring comprising 1-3 heteroatoms selected from N, O, and S, wherein the phenyl, heterocyclic, or heteroaryl is optionally substituted with one or more $R_{15}$; and each $R_{15}$ is independently $(C_1-C_6)$ alkyl, $(C_1-C_6)$ haloalkyl, $(C_1-C_6)$ alkoxy, OH, $NH_2$, $NH(C_1-C_6)$ alkyl, $N((C_1-C_6)$ alkyl$)_2$, or halogen.

(1a) In some embodiments of Formula (I), two of $Z_1$, $Z_2$, and $Z_3$ are N, and the remaining $Z_1$, $Z_2$, and $Z_3$ are $CR_8$. In some embodiments, $Z_1$ and $Z_2$ are N. In other embodiments, $Z_1$ and $Z_3$ are N. In other embodiments, $Z_2$ and $Z_3$ are N.

(1b) In some embodiments of Formula (I), $Z_1$, $Z_2$, and $Z_3$ are each N.

(2a) In some embodiments of Formula (I), $R_8$ is H or halogen (e.g., F, Cl, Br, or I). In further embodiments, $R_8$ is H. In other embodiments, $R_8$ is halogen. In further embodiments, $R_8$ is Cl.

(2b) In some embodiments of Formula (I), $R_8$ is $(C_1-C_4)$ alkyl (e.g., methyl, ethyl, propyl, i-propyl, or butyl).

(2c) In some embodiments of Formula (I), $R_8$ is $(C_1-C_4)$ haloalkyl (e.g., $CH_2F$, $CHF_2$, or $CF_3$).

(3a) In some embodiments of Formula (I), $R_1$ is H, $NH_2$, $NH(C_1-C_4)$ alkyl, or $N((C_1-C_4)$ alkyl$)_2$. In further embodiments, $R_1$ is H or $NH_2$. In other embodiments, $R_1$ is $NH(C_1-C_4)$ alkyl (e.g., methylamino, ethylamino, propylamino, or butylamino) or $N((C_1-C_4)$ alkyl$)_2$ (e.g., dimethylamino, diethylamino, dipropylamino, or dibutylamino).

(3b) In some embodiments of Formula (I), $R_1$ is $(C_1-C_4)$ alkyl (e.g., methyl, ethyl, propyl, i-propyl, or butyl).

(3c) In some embodiments of Formula (I), $R_1$ is $(C_1-C_4)$ haloalkyl (e.g., $CH_2F$, $CHF_2$, or $CF_3$).

(3d) In some embodiments of Formula (I), $R_1$ is halogen (e.g., F, Cl, Br, or I). In further embodiments; $R_1$ is Cl.

(4a) In some embodiments of Formula (I), $R_2$ is H.

(4b) In some embodiments of Formula (I), $R_2$ is $(C_1-C_6)$ alkyl (e.g., methyl, ethyl, propyl, i-propyl, butyl, i-butyl, s-butyl, t-butyl, pentyl, or hexyl).

(5a) In some embodiments of Formula (I), $R_3$ is $(C_1-C_4)$ alkoxy (e.g., methoxy, ethoxy, propoxy, or butoxy). In further embodiments, $R_3$ is methoxy.

(5b) In some embodiments of Formula (I), $R_3$ is $(C_1-C_4)$ alkyl (e.g., methyl, ethyl, propyl, i-propyl, or butyl).

(5c) In some embodiments of Formula (I), $R_3$ is $(C_1-C_4)$ haloalkyl (e.g., $CH_2F$, $CHF_2$, or $CF_3$).

(5d) In some embodiments of Formula (I), $R_3$ is halogen (e.g., F, Cl, Br, or I).

(6a) In some embodiments of Formula (I), $R_4$ is $NR_9R_{10}$.

(6a1) In some embodiments of Formula (I), $R_9$ is H.

(6a2) In some embodiments of Formula (I), $R_9$ is $(C_1-C_4)$ alkyl (e.g., methyl, ethyl, propyl, i-propyl, or butyl). In further embodiments, $R_9$ is methyl.

(6a3) In some embodiments of Formula (I), $R_{10}$ is $(C_1-C_4)$ alkyl (e.g., methyl, ethyl, propyl, i-propyl, or butyl).

(6a4) In some embodiments of Formula (I), $R_{10}$ is $(C_1-C_4)$ alkyl-$NH(C_1-C_4)$ alkyl, wherein in each instance, $(C_1-C_4)$ alkyl is independently selected from methyl, ethyl, propyl, i-propyl, and butyl.

(6a5) In some embodiments of Formula (I), $R_{10}$ is $(C_1-C_4)$ alkyl-$N((C_1-C_4)$ alkyl$)_2$, wherein in each instance, $(C_1-C_4)$ alkyl is independently selected from methyl, ethyl, propyl, i-propyl, and butyl.

(6a6) In some embodiments of Formula (I), $R_9$ and $R_{10}$ together with the nitrogen atom to which they are attached form a 5- to 7-membered heterocycle optionally comprising 1 or 2 additional heteroatoms selected from N, O, and S and optionally substituted with one or more $R_{11}$. In further embodiments, $R_9$ and $R_{10}$ together with the nitrogen atom to which they are attached form a 6-membered heterocycle optionally comprising 1 or 2 additional heteroatoms selected from N, O, and S. In further embodiments, $R_9$ and $R_{10}$ together with the nitrogen atom to which they are attached form a piperidine or piperazine.

(6a7) In some embodiments of Formula (I), each $R_{11}$ is independently $(C_1-C_4)$ alkyl (e.g., methyl, ethyl, propyl, i-propyl, or butyl), $(C_1-C_4)$ haloalkyl (e.g., $CH_2F$, $CHF_2$, or $CF_3$), $(C_1-C_4)$ alkoxy (e.g., methoxy, ethoxy, propoxy, or butoxy), or halogen (e.g., F, Cl, Br, or I). In further embodiments, $R_{11}$ is N-methyl.

(6b) In some embodiments of Formula (I), $R_4$ is a 5- to 7-membered heterocycle comprising 1-3 heteroatoms selected from N, O, and S and optionally substituted with one or more $R_{11}$. In further embodiments, $R_4$ is a 6-membered heterocycle comprising 1-3 heteroatoms selected from N, O, and S and optionally substituted with one or more $R_{11}$.

(6b1) In some embodiments of Formula (I), each $R_{11}$ is independently $(C_1-C_4)$ alkyl (e.g., methyl, ethyl, propyl, i-propyl, or butyl), $(C_1-C_4)$ haloalkyl (e.g., $CH_2F$, $CHF_2$, or $CF_3$), $(C_1-C_4)$ alkoxy (e.g., methoxy, ethoxy, propoxy, or butoxy), or halogen (e.g., F, Cl, Br, or I).

(7a) In some embodiments of Formula (I), $R_5$ is $NR_{12}C(O)R_{13}$.

(7a1) In some embodiments of Formula (I), $R_{12}$ is H, and $R_{13}$ is $(C_1-C_4)$ alkyl (e.g., methyl, ethyl, propyl, i-propyl, or butyl) or $(C_2-C_6)$ alkenyl (e.g., ethenyl, propenyl, butenyl, pentenyl, or hexenyl), wherein the alkyl or alkenyl is optionally substituted with one or more substituents independently selected from halogen, OH, CN, and $NH_2$. In further embodiments, $R_{12}$ is H, and $R_{13}$ is $(C_2-C_6)$ alkenyl (e.g., ethenyl, propenyl, butenyl, pentenyl, or hexenyl), wherein the alkenyl is optionally substituted with one or more substituents independently selected from halogen, OH, CN, and $NH_2$.

(7a2) In some embodiments of Formula (I), $R_{12}$ is $(C_1-C_4)$ alkyl (e.g., methyl, ethyl, propyl, i-propyl, or butyl), and $R_{13}$ is $(C_1-C_4)$ alkyl (e.g., methyl, ethyl, propyl, i-propyl, or butyl) or $(C_2-C_6)$ alkenyl (e.g., ethenyl, propenyl, butenyl, pentenyl, or hexenyl), wherein the alkyl or alkenyl is optionally substituted with one or more substituents independently selected from halogen, OH, CN, and $NH_2$. In further embodiments, $R_{12}$ is $(C_1-C_4)$ alkyl (e.g., methyl, ethyl, propyl, i-propyl, or butyl), and $R_{13}$ is $(C_2-C_6)$ alkenyl (e.g., ethenyl, propenyl, butenyl, pentenyl, or hexenyl), wherein the alkenyl is optionally substituted with one or more substituents independently selected from halogen, OH, CN, and $NH_2$.

(7b) In some embodiments of Formula (I), $R_5$ is $C(O)NR_{12}R_{13}$.

(7b1) In some embodiments of Formula (I), $R_{12}$ is H, and $R_{13}$ is $(C_1-C_4)$ alkyl (e.g., methyl, ethyl, propyl, i-propyl, or butyl) or $(C_2-C_6)$ alkenyl (e.g., ethenyl, propenyl, butenyl, pentenyl, or hexenyl), wherein the alkyl or alkenyl is optionally substituted with one or more substituents independently selected from halogen, OH, CN, and $NH_2$. In further embodiments, $R_{12}$ is H, and $R_{13}$ is $(C_2-C_6)$ alkenyl (e.g., ethenyl, propenyl, butenyl, pentenyl, or hexenyl), wherein the alkenyl is optionally substituted with one or more substituents independently selected from halogen, OH, CN, and $NH_2$.

(7b2) In some embodiments of Formula (I), $R_{12}$ is $(C_1-C_4)$ alkyl (e.g., methyl, ethyl, propyl, i-propyl, or butyl), and $R_{13}$ is $(C_1-C_4)$ alkyl (e.g., methyl, ethyl, propyl, i-propyl, or butyl) or $(C_2-C_6)$ alkenyl (e.g., ethenyl, propenyl, butenyl, pentenyl, or hexenyl), wherein the alkyl or alkenyl is optionally substituted with one or more substituents independently selected from halogen, OH, CN, and $NH_2$. In further embodiments, $R_{12}$ is $(C_1-C_4)$ alkyl (e.g., methyl, ethyl, propyl, i-propyl, or butyl), and $R_{13}$ is $(C_2-C_6)$ alkenyl (e.g., ethenyl, propenyl, butenyl, pentenyl, or hexenyl), wherein the alkenyl is optionally substituted with one or more substituents independently selected from halogen, OH, CN, and $NH_2$.

(8a) In some embodiments of Formula (I), $R_6$ and $R_7$ together with the nitrogen atom to which they are attached form a 5- or 6-membered heterocyclic ring (pyrrolidine, pyrazolidine, imidazolidine, triazolidine, oxazolidine, isoxazolidine, oxadiazolidine, dioxazolidine, thiazolidine, isothiazolidine, thiadiazolidine, dithiazolidine, piperidine, hexahydropyridazine, hexahydropyrimidine, morpholine, etc.). In further embodiments, $R_6$ and $R_7$ together with the nitrogen atom to which they are attached form a 5-membered heterocyclic ring.

(8b) In some embodiments of Formula (I), $R_6$ and $R_7$ together with the nitrogen atom to which they are attached form a 5- or 6-membered heteroaryl ring (pyrrole, pyrazole, imidazole, triazole, oxazole, isoxazole, oxadiazole, dioxazole, thiazole, isothiazole, thiadiazole, dithiazole, pyridine, pyridazine, pyrimidine, triazine, etc.). In further embodiments, $R_6$ and $R_7$ together with the nitrogen atom to which they are attached form a 5-membered heteroaryl ring. In further embodiments, $R_6$ and $R_7$ together with the nitrogen atom to which they are attached form pyrrole, pyrazole or imidazole.

(9a) In some embodiments of Formula (I), each $R_{14}$ is independently $(C_1-C_4)$ alkyl (e.g., methyl, ethyl, propyl, i-propyl, or butyl), $(C_1-C_4)$ haloalkyl (e.g., $CH_2F$, $CHF_2$, or $CF_3$), $(C_1-C_4)$ alkoxy (e.g., methoxy, ethoxy, propoxy, or butoxy), halogen (e.g., F, Cl, Br, or I), OH, $NH(C_1-C_4)$ alkyl (e.g., methylamino, ethylamino, propylamino, or butylamino), or $N((C_1-C_4)$ alkyl$)_2$ (e.g., dimethylamino, diethylamino, dipropylamino, or dibutylamino). In further embodiments, each $R_{14}$ is independently $(C_1-C_4)$ alkyl (e.g., methyl, ethyl, propyl, i-propyl, or butyl) or $(C_1-C_4)$ haloalkyl (e.g., $CH_2F$, $CHF_2$, or $CF_3$). In further embodiments, each $R_{14}$ is independently methyl or $CF_3$.

(9b) In some embodiments of Formula (I), two $R_{14}$ together with the atoms to which they are attached form a phenyl ring or a 5- or 6-membered heterocyclic or heteroaryl ring comprising 1-3 heteroatoms selected from N, O, and S, wherein the phenyl, heterocyclic, or heteroaryl is optionally substituted with one or more $R_{15}$.

(9b1) In further embodiments, two $R_{14}$ together with the atoms to which they are attached form a phenyl ring.

(9b2) In other embodiments, two $R_{14}$ together with the atoms to which they are attached form a 5- or 6-membered heterocyclic ring (pyrrolidine, pyrazolidine, imidazolidine, triazolidine, oxazolidine, isoxazolidine, oxadiazolidine, dioxazolidine, thiazolidine, isothiazolidine, thiadiazolidine, dithiazolidine, piperidine, hexahydropyridazine, hexahydropyrimidine, morpholine, etc.).

(9b3) In other embodiments, two $R_{14}$ together with the atoms to which they are attached form a 5- or 6-membered heteroaryl ring (pyrrole, pyrazole, imidazole, triazole, oxazole, isoxazole, oxadiazole, dioxazole, thiazole, isothiazole, thiadiazole, dithiazole, pyridine, pyridazine, pyrimidine, triazine, etc.). In further embodiments, two $R_{14}$ together with the atoms to which they are attached form a 6-membered heteroaryl ring. In further embodiments, two $R_{14}$ together with the atoms to which they are attached form pyridine.

(10) In some embodiments of Formula (I), each $R_{15}$ is independently $(C_1\text{-}C_4)$ alkyl (e.g., methyl, ethyl, propyl, i-propyl, or butyl), $(C_1\text{-}C_4)$ haloalkyl (e.g., $CH_2F$, $CHF_2$, or $CF_3$), $(C_1\text{-}C_4)$ alkoxy (e.g., methoxy, ethoxy, propoxy, or butoxy), halogen (e.g., F, Cl, Br, or I), OH, $NH(C_1\text{-}C_4)$ alkyl (e.g., methylamino, ethylamino, propylamino, or butylamino), or $N((C_1\text{-}C_4) \text{ alkyl})_2$ (e.g., dimethylamino, diethylamino, dipropylamino, or dibutylamino). In further embodiments, each $R_{15}$ is independently $(C_1\text{-}C_4)$ alkyl (e.g., methyl, ethyl, propyl, i-propyl, or butyl) or $(C_1\text{-}C_4)$ haloalkyl (e.g., $CH_2F$, $CHF_2$, or $CF_3$). In further embodiments, each $R_{15}$ is independently methyl or $CF_3$.

In some embodiments of Formula (I), each of the substituents defined for any one of $Z_1$, $Z_2$, $Z_3$, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ can be combined with any of the substituents defined for the remainder of $Z_1$, $Z_2$, $Z_3$, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$.

(11) In some embodiments of Formula (I), $Z_1$, $Z_2$, and $Z_3$ are defined as in (1a) or (1b), and $R_8$ is as defined in (2a).

(12) In some embodiments of Formula (I), $Z_1$, $Z_2$, and $Z_3$ are defined as in (1a) or (1b), and $R_1$ is as defined in (3a).

(13) In some embodiments of Formula (I), $Z_1$, $Z_2$, and $Z_3$ are defined as in (1a) or (1b), and $R_3$ is as defined in (5a).

(14) In some embodiments of Formula (I), $Z_1$, $Z_2$, and $Z_3$ are defined as in (1a) or (1b), and $R_4$ is as defined in (6a).

(15) In some embodiments of Formula (I), $Z_1$, $Z_2$, and $Z_3$ are defined as in (1a) or (1b), $R_4$ is as defined in (6a), and $R_9$ and $R_{10}$ are defined as in (6a2)-(6a5).

(16) In some embodiments of Formula (I), $Z_1$, $Z_2$, and $Z_3$ are defined as in (1a) or (1b), $R_4$ is as defined in (6a), and $R_9$ and $R_{10}$ are defined as in (6a6).

(17) In some embodiments of Formula (I), $Z_1$, $Z_2$, and $Z_3$ are defined as in (1a) or (1b), and $R_5$ is as defined in (7a).

(18) In some embodiments of Formula (I), $Z_1$, $Z_2$, and $Z_3$ are defined as in (1a) or (1b), $R_5$ is as defined in (7a), and $R_{12}$ and $R_{13}$ are defined as in (7a1)-(7a2).

(19) In some embodiments of Formula (I), $Z_1$, $Z_2$, and $Z_3$ are defined as in (1a) or (1b), and $R_5$ is as defined in (7b).

(20) In some embodiments of Formula (I), $Z_1$, $Z_2$, and $Z_3$ are defined as in (1a) or (1b), $R_5$ is as defined in (7b), and $R_{12}$ and $R_{13}$ are defined as in (7b1)-(7b2).

(21) In some embodiments of Formula (I), $R_6$ and $R_7$ are defined as in (8a) or (8b), and $R_{14}$ is as defined in (9b).

(22) In some embodiments of Formula (I), $Z_1$, $Z_2$, $Z_3$, $R_3$, $R_4$, $R_5$, $R_6$, and $R_7$ are as defined in (13), (14), (17), and (21).

In one embodiment, the compounds of Formula (I) have the structure of Formula (Ia), (Ib), or (Ic):

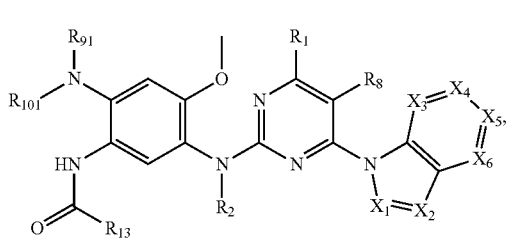

(Ia)

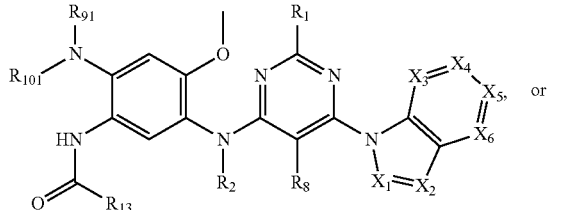

(Ib)

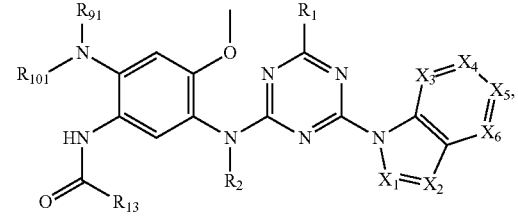

(Ic)

or pharmaceutically acceptable salts, hydrates, solvates, prodrugs, stereoisomers, or tautomers thereof, wherein:

$X_1$, $X_2$, $X_3$, $X_4$, $X_5$ and $X_6$ are each independently N or $CR_{15}$;

each $R_{15}$ is independently $(C_1\text{-}C_6)$ alkyl, $(C_1\text{-}C_6)$ haloalkyl, $(C_1\text{-}C_6)$ alkoxy, OH, $NH_2$, $NH(C_1\text{-}C_6)$ alkyl, $N((C_1\text{-}C_6) \text{ alkyl})_2$, or halogen;

$R_1$ is H, $(C_1\text{-}C_4)$ alkyl, $(C_1\text{-}C_4)$ haloalkyl, $NH_2$, $NH(C_1\text{-}C_4)$ alkyl, $N((C_1\text{-}C_4) \text{ alkyl})_2$, or halogen;

$R_2$ is H or $(C_1\text{-}C_6)$ alkyl;

$R_8$ is H, $(C_1\text{-}C_4)$ alkyl, $(C_1\text{-}C_4)$ haloalkyl, or halogen;

$R_{91}$ is $(C_1\text{-}C_4)$ alkyl;

$R_{101}$ is $(C_1\text{-}C_4)$ alkyl-$NH(C_1\text{-}C_4)$ alkyl or $(C_1\text{-}C_4)$ alkyl-$N((C_1\text{-}C_4) \text{ alkyl})_2$;

or $R_{91}$ and $R_{101}$ together with the nitrogen atom to which they are attached form a 5- to 7-membered heterocycle optionally comprising 1 or 2 additional heteroatoms selected from N, O, and S and optionally substituted with one or more $R_{11}$;

each $R_{11}$ is independently $(C_1\text{-}C_4)$ alkyl, $(C_1\text{-}C_4)$ haloalkyl, $(C_1\text{-}C_4)$ alkoxy, or halogen; and $R_{13}$ is $(C_1\text{-}C_6)$ alkyl or $(C_2\text{-}C_6)$ alkenyl, wherein the alkyl or alkenyl is optionally substituted with one or more substituents independently selected from halogen, OH, CN, and $NH_2$.

(23a) In some embodiments of Formulae (Ia)-(Ic), $R_8$ is H or halogen (e.g., F, Cl, Br, or I). In further embodiments, $R_8$ is H. In other embodiments, $R_8$ is halogen. In further embodiments, $R_8$ is Cl.

(23b) In some embodiments of Formulae (Ia)-(Ic), $R_8$ is $(C_1\text{-}C_4)$ alkyl (e.g., methyl, ethyl, propyl, i-propyl, or butyl).

(23c) In some embodiments of Formulae (Ia)-(Ic), $R_8$ is $(C_1\text{-}C_4)$ haloalkyl (e.g., $CH_2F$, $CHF_2$, or $CF_3$).

(24a) In some embodiments of Formulae (Ia)-(Ic), $R_1$ is H, $NH_2$, $NH(C_1\text{-}C_4)$ alkyl, or $N((C_1\text{-}C_4) \text{ alkyl})_2$. In further embodiments, $R_1$ is H or $NH_2$. In other embodiments, $R_1$ is $NH(C_1\text{-}C_4)$ alkyl (e.g., methylamino, ethylamino, propylamino, or butylamino) or $N((C_1\text{-}C_4) \text{ alkyl})_2$ (e.g., dimethylamino, diethylamino, dipropylamino, or dibutylamino).

(24b) In some embodiments of Formulae (Ia)-(Ic), $R_1$ is $(C_1\text{-}C_4)$ alkyl (e.g., methyl, ethyl, propyl, i-propyl, or butyl).

(24c) In some embodiments of Formulae (Ia)-(Ic), $R_1$ is $(C_1\text{-}C_4)$ haloalkyl (e.g., $CH_2F$, $CHF_2$, or $CF_3$).

(24d) In some embodiments of Formulae (Ia)-(Ic), $R_1$ is halogen (e.g., F, Cl, Br, or I). In further embodiments; $R_1$ is Cl.

(25a) In some embodiments of Formulae (Ia)-(Ic), $R_2$ is H.

(25b) In some embodiments of Formulae (Ia)-(Ic), $R_2$ is $(C_1-C_6)$ alkyl (e.g., methyl, ethyl, propyl, i-propyl, butyl, i-butyl, s-butyl, t-butyl, pentyl, or hexyl).

(26a1) In some embodiments of Formulae (Ia)-(Ic), $R_{91}$ is $(C_1-C_4)$ alkyl. (e.g., methyl, ethyl, propyl, i-propyl, or butyl). In further embodiments, $R_{91}$ is methyl.

(26a2) In some embodiments of Formulae (Ia)-(Ic), $R_{101}$ is $(C_1-C_4)$ alkyl-NH$(C_1-C_4)$ alkyl, wherein in each instance, $(C_1-C_4)$ alkyl is independently selected from methyl, ethyl, propyl, i-propyl, and butyl.

(26a3) In some embodiments of Formulae (Ia)-(Ic), $R_{101}$ is $(C_1-C_4)$ alkyl-N$((C_1-C_4)$ alkyl$)_2$, wherein in each instance, $(C_1-C_4)$ alkyl is independently selected from methyl, ethyl, propyl, i-propyl, and butyl.

(26a4) In some embodiments of Formulae (Ia)-(Ic), $R_{91}$ and $R_{101}$ together with the nitrogen atom to which they are attached form a 5- to 7-membered heterocycle optionally comprising 1 or 2 additional heteroatoms selected from N, O, and S and optionally substituted with one or more $R_{11}$. In further embodiments, $R_{91}$ and $R_{101}$ together with the nitrogen atom to which they are attached form a 6-membered heterocycle optionally comprising 1 or 2 additional heteroatoms selected from N, O, and S. In further embodiments, $R_{91}$ and $R_{101}$ together with the nitrogen atom to which they are attached form a piperidine or piperazine.

(26a5) In some embodiments of Formulae (Ia)-(Ic), each $R_{11}$ is independently $(C_1-C_4)$ alkyl (e.g., methyl, ethyl, propyl, i-propyl, or butyl), $(C_1-C_4)$ haloalkyl (e.g., $CH_2F$, $CHF_2$, or $CF_3$), $(C_1-C_4)$ alkoxy (e.g., methoxy, ethoxy, propoxy, or butoxy), or halogen (e.g., F, Cl, Br, or I). In further embodiments, $R_{11}$ is N-methyl.

(27) In some embodiments of Formulae (Ia)-(Ic), $R_{13}$ is $(C_1-C_4)$ alkyl (e.g., methyl, ethyl, propyl, i-propyl, or butyl) or $(C_2-C_6)$ alkenyl (e.g., ethenyl, propenyl, butenyl, pentenyl, or hexenyl), wherein the alkyl or alkenyl is optionally substituted with one or more substituents independently selected from halogen, OH, CN, and $NH_2$. In further embodiments, $R_{13}$ is $(C_2-C_6)$ alkenyl (e.g., ethenyl, propenyl, butenyl, pentenyl, or hexenyl), wherein the alkenyl is optionally substituted with one or more substituents independently selected from halogen, OH, CN, and $NH_2$.

(28) In some embodiments of Formulae (Ia)-(Ic), each $R_{15}$ is independently $(C_1-C_4)$ alkyl (e.g., methyl, ethyl, propyl, i-propyl, or butyl), $(C_1-C_4)$ haloalkyl (e.g., $CH_2F$, $CHF_2$, or $CF_3$), $(C_1-C_4)$ alkoxy (e.g., methoxy, ethoxy, propoxy, or butoxy), halogen (e.g., F, Cl, Br, or I), OH, NH$(C_1-C_4)$ alkyl (e.g., methylamino, ethylamino, propylamino, or butylamino), or N$((C_1-C_4)$ alkyl$)_2$ (e.g., dimethylamino, diethylamino, dipropylamino, or dibutylamino). In further embodiments, each $R_{15}$ is independently $(C_1-C_4)$ alkyl (e.g., methyl, ethyl, propyl, i-propyl, or butyl) or $(C_1-C_4)$ haloalkyl (e.g., $CH_2F$, $CHF_2$, or $CF_3$). In further embodiments, each $R_{15}$ is independently methyl or $CF_3$.

In some embodiments of Formulae (Ia)-(Ic), $R_8$ is defined as in (23a) and $R_1$ is as defined in (24a).

In some embodiments of Formulae (Ia)-(Ic), $R_8$ is defined as in (23a), $R_1$ is as defined in (24a), and $R_2$ is as defined in (25a).

In some embodiments of Formulae (Ia)-(Ic), $R_8$ is defined as in (23a), $R_1$ is as defined in (24a), $R_2$ is as defined in (25a), and $R_{13}$ is as defined in (27).

In some embodiments of Formulae (Ia)-(Ic), $R_8$ is defined as in (23a), $R_1$ is as defined in (24a), $R_2$ is as defined in (25a), $R_{13}$ is as defined in (27), $R_{91}$ is as defined in (26a1) and $R_{101}$ is as defined in (26a2).

In some embodiments of Formulae (Ia)-(Ic), $R_8$ is defined as in (23a), $R_1$ is as defined in (24a), $R_2$ is as defined in (25a), $R_{13}$ is as defined in (27), $R_{91}$ is as defined in (26a1) and $R_{101}$ is as defined in (26a3).

In some embodiments of Formulae (Ia)-(Ic), $R_8$ is defined as in (23a), $R_1$ is as defined in (24a), $R_2$ is as defined in (25a), $R_{13}$ is as defined in (27), $R_{91}$ and $R_{101}$ are as defined in (26a4) and $R_{11}$ is as defined in (26a5).

In some embodiments of Formulae (Ia)-(Ic), each of the substituents defined for any one of $R_1$, $R_2$, $R_8$, $R_{91}$, $R_{101}$, $R_{11}$, $R_{13}$, and $R_{15}$ can be combined with any of the substituents defined for the remainder of $R_1$, $R_2$, $R_8$, $R_{91}$, $R_{10}$, $R_{11}$, $R_{13}$, and $R_{15}$.

In some embodiments of the Formulae (Ia)-(Ic),

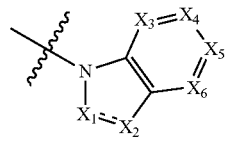

is selected from:

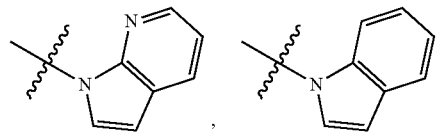

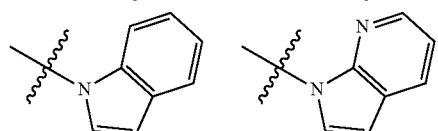

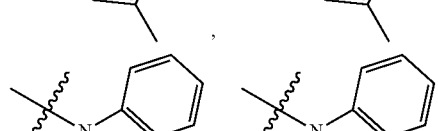

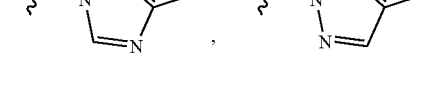

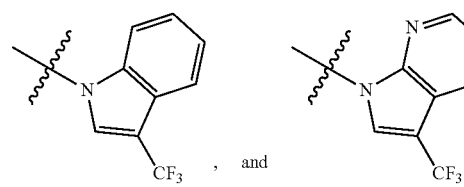

Non-limiting illustrative compounds of the application include:

| Compound Number | Structure | Compound Name |
|---|---|---|
| I-1 | 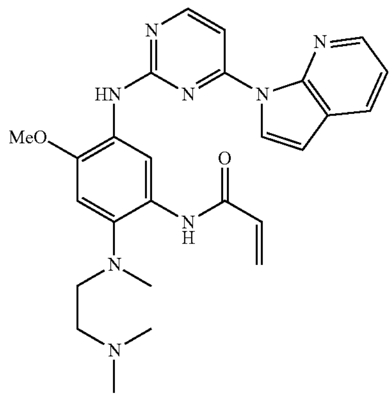 [SMILES: C=CC(=O)Nc1cc(Nc2nccc(-n3ccc4cccnc43)n2)c(OC)cc1N(C)CCN(C)C] | N-(5-((4-(1H-pyrrolo[2,3-b]pyridin-1-yl)pyrimidin-2-yl)amino)-2-((2-(dimethylamino)ethyl)(methyl)amino)-4-methoxyphenyl)acrylamide |
| I-2 | 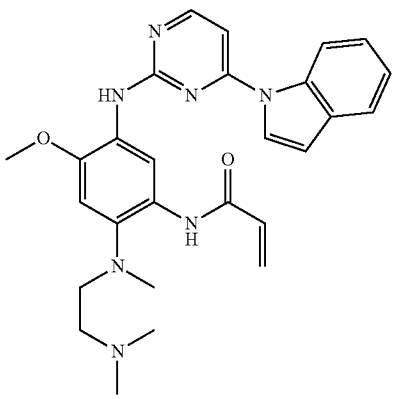 [SMILES: C=CC(=O)Nc1cc(Nc2nccc(-n3ccc4ccccc43)n2)c(OC)cc1N(C)CCN(C)C] | N-(5-((4-(1H-indol-1-yl)pyrimidin-2-yl)amino)-2-((2-(dimethylamino)ethyl)(methyl)amino)-4-methoxyphenyl)acrylamide |
| I-3 | 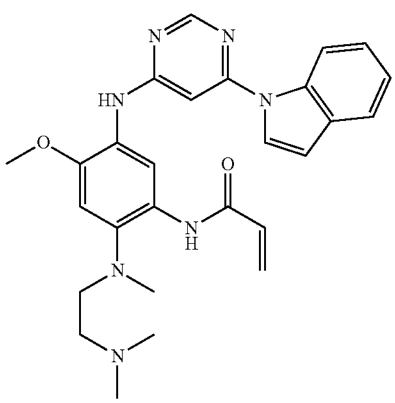 [SMILES: C=CC(=O)Nc1cc(Nc2cc(-n3ccc4ccccc43)ncn2)c(OC)cc1N(C)CCN(C)C] | N-(5-((6-(1H-indol-1-yl)pyrimidin-4-yl)amino)-2-((2-(dimethylamino)ethyl)(methyl)amino)-4-methoxyphenyl)acrylamide |
| I-4 | 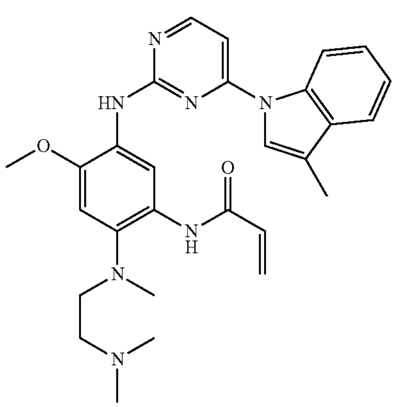 [SMILES: C=CC(=O)Nc1cc(Nc2nccc(-n3cc(C)c4ccccc43)n2)c(OC)cc1N(C)CCN(C)C] | N-(2-((2-(dimethylamino)ethyl)(methyl)amino)-4-methoxy-5-((4-(3-methyl-1H-indol-1-yl)pyrimidin-2-yl)amino)phenyl)acrylamide |

-continued

| Compound Number | Structure | Compound Name |
|---|---|---|
| I-5 | 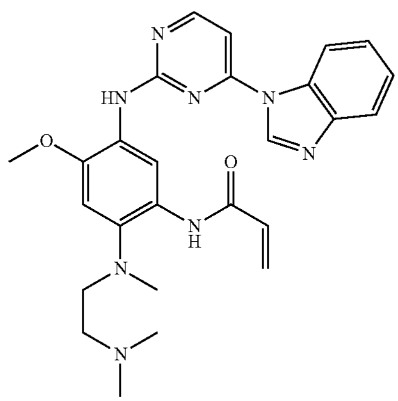 [SMILES: C=CC(=O)Nc1cc(Nc2nccc(-n3cnc4ccccc43)n2)c(OC)cc1N(C)CCN(C)C] | N-(5-((4-(1H-benzo[d]imidazol-1-yl)pymidin-2-yl)amino)-2-((2-(dimethylamino)ethyl)(methyl)amino)-4-methoxyphenyl)acrylamide |
| I-6 | 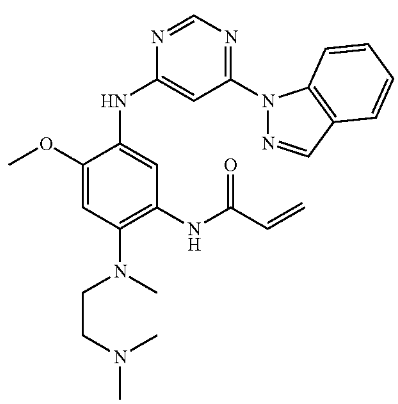 [SMILES: C=CC(=O)Nc1cc(Nc2cc(-n3ncc4ccccc43)ncn2)c(OC)cc1N(C)CCN(C)C] | N-(5-((6-(1H-indazol-1-yl)pyrimidin-4-yl)amino)-2-((2-(dimethylamino)ethyl)(methyl)amino)-4-methoxyphenyl)acrylamide |
| I-7 | 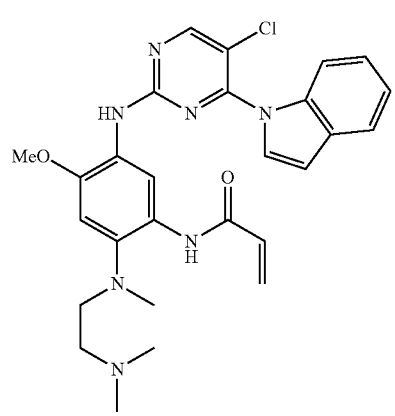 [SMILES: C=CC(=O)Nc1cc(Nc2ncc(Cl)c(-n3ccc4ccccc43)n2)c(OC)cc1N(C)CCN(C)C] | N-(5-((5-chloro-4-(1H-indol-1-yl)pyrimidin-2-yl)amino)-2-((2-(dimethylamino)ethyl)(methyl)amino)-4-methoxyphenyl)acrylamide |

-continued

| Compound Number | Structure | Compound Name |
|---|---|---|
| I-8 | 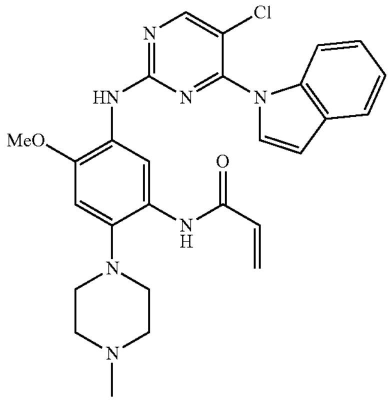 [SMILES: C=CC(=O)Nc1cc(Nc2ncc(Cl)c(-n3ccc4ccccc43)n2)c(OC)cc1N1CCN(C)CC1] | N-(5-((5-chloro-4-(1H-indol-1-yl)pyrimidin-2-yl)amino)-4-methoxy-2-(4-methylpiperazin-1-yl)phenyl)acrylamide |
| I-9 | 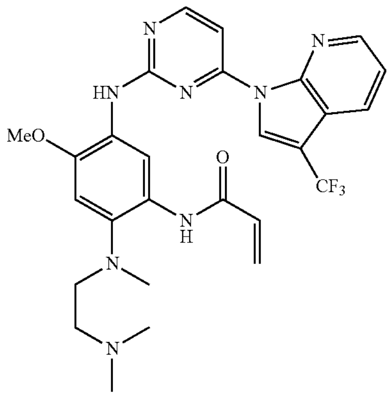 | N-(2-((2-(dimethylamino)ethyl)(methyl)amino)-4-methoxy-5-((4-(3-(trifluoromethyl)-1H-pyrrolo[2,3-b]pyridin-1-yl)pyrimidin-2-yl)amino)phenyl)acrylamide |
| I-10 | 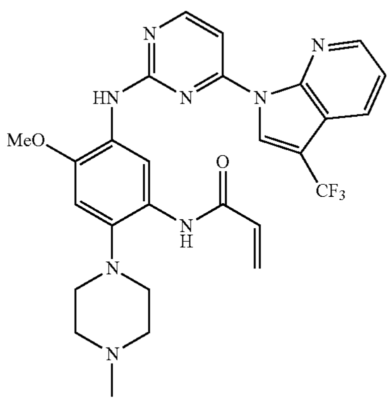 | N-(4-methoxy-2-(4-methylpiperazin-1-yl)-5-((4-(3-(trifluoromethyl)-1H-pyrrolo[2,3-b]pyridin-1-yl)pyrimidin-2-yl)amino)phenyl)acrylamide |
| I-11 | 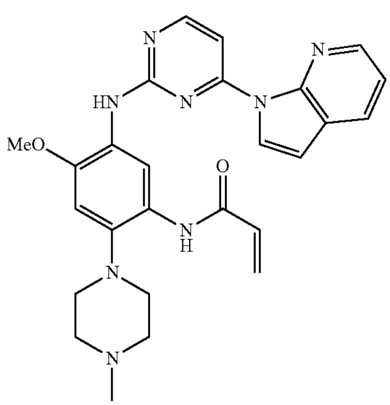 | N-(5-((4-(1H-pyrrolo[2,3-b]pyridin-1-yl)pyrimidin-2-yl)amino)-4-methoxy-2-(4-methylpiperazin-1-yl)phenyl)acrylamide |

-continued

| Compound Number | Structure | Compound Name |
|---|---|---|
| I-12 | 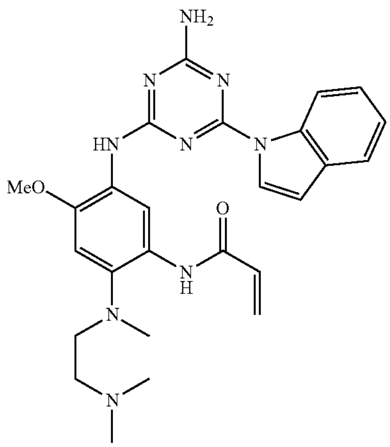 | N-(5-((4-amino-6-(1H-indol-1-yl)-1,3,5-triazin-2-yl)amino)-2-((2-(dimethylamino)ethyl)(methyl)amino)-4-methoxyphenyl)acrylamide |
| I-13 | 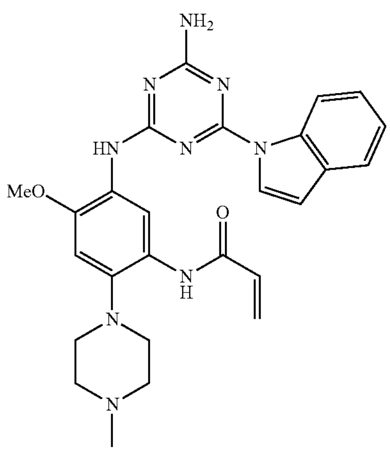 | N-(5-((4-amino-6-(1H-indol-1-yl)-1,3,5-triazin-2-yl)amino)-4-methoxy-2-(4-methylpiperazin-1-yl)phenyl)acrylamide |
| I-14 | 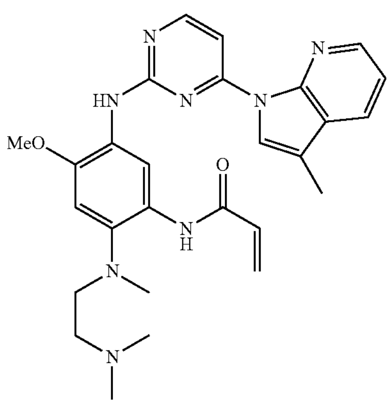 [SMILES: C=CC(=O)Nc1cc(Nc2nccc(-n3cc(C)c4cccnc43)n2)c(OC)cc1N(C)CCN(C)C] | N-(2-((2-(dimethylamino)ethyl)(methyl)amino)-4-methoxy-5-((4-(3-methyl-1H-pyrrolo[2,3-b]pyridin-1-yl)pyrimidin-2-yl)amino)phenyl)acrylamide |

| Compound Number | Structure | Compound Name |
|---|---|---|
| I-15 | 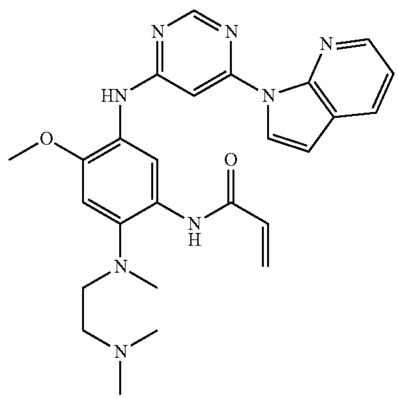 [SMILES: C=CC(=O)Nc1cc(Nc2cc(-n3ccc4cccnc43)ncn2)c(OC)cc1N(C)CCN(C)C] | N-(5-((6-(1H-pyrrolo[2,3-b]pyridin-1-yl)pyrimidin-4-yl)amino)-2-((2-(dimethylamino)ethyl)(methyl)amino)-4-methoxyphenyl)acrylamide |
| I-16 | 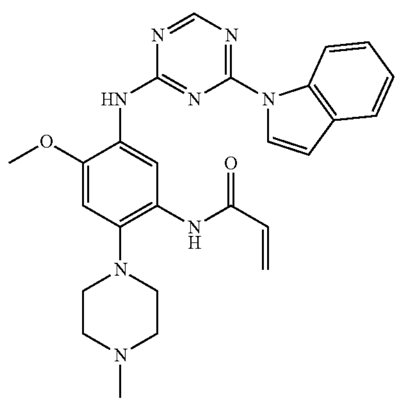 [SMILES: C=CC(=O)Nc1cc(Nc2ncnc(-n3ccc4ccccc43)n2)c(OC)cc1N1CCN(C)CC1] | N-(5-((4-(1H-indol-1-yl)-1,3,5-triazin-2-yl)amino)-4-methoxy-2-(4-methylpiperazin-1-yl)phenyl)acrylamide |
| I-17 | 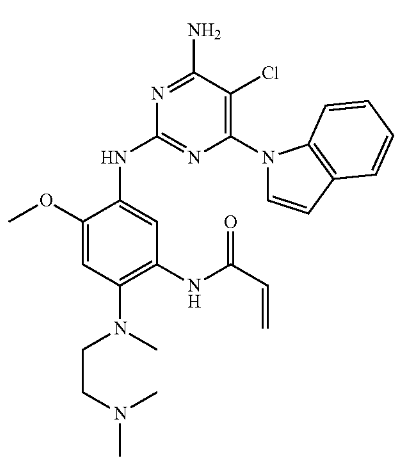 [SMILES: C=CC(=O)Nc1cc(Nc2nc(N)c(Cl)c(-n3ccc4ccccc43)n2)c(OC)cc1N(C)CCN(C)C] | N-(5-((4-amino-5-chloro-6-(1H-indol-1-yl)pyrimidin-2-yl)amino)-2-((2-(dimethylamino)ethyl)(methyl)amino)-4-methoxyphenyl)acrylamide |

| Compound Number | Structure | Compound Name |
| --- | --- | --- |
| I-18 | 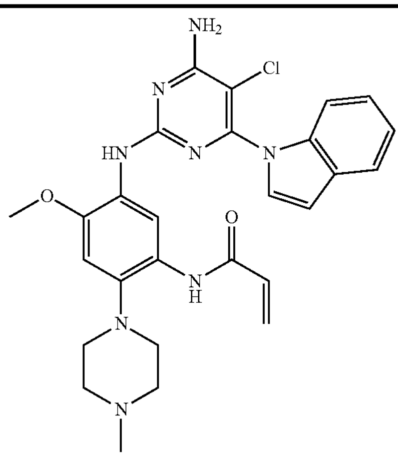 | N-(5-((4-amino-5-chloro-6-(1H-indol-1-yl)pyrimidin-2-yl)amino)-4-methoxy-2-(4-methylpiperazin-1-yl)phenyl)acrylamide |

The compounds of the application are capable of modulating EGFR activity. In one embodiment, the compounds of the present application are capable of inhibiting or decreasing EGFR activity.

In one embodiment, the compounds of the present application are capable of modulating (e.g., inhibiting or decreasing) the activity of EGFR containing one or more mutations. In one embodiment, the mutant EGFR contains one or more mutations selected from T790M, L718Q, L844V, L858R, and Del. In one embodiment, the mutant EGFR contains a combination of mutations, wherein the combination is selected from Del/L718Q, Del/L844V, Del/T790M, Del/T790M/L718Q, Del/T790M/L844V, L858R/L718Q, L858R/L844V, L858R/T790M, and L858R/T790M/L718Q. In one embodiment, the mutant EGFR contains a combination of mutations, wherein the combination is selected from Del/L718Q, Del/L844V, Del/T790M, Del/T790M/L844V, L858R/L844V, and L858R/T790M. In one embodiment, the mutant EGFR contains a combination of mutations, wherein the combination is selected from L858R/T790M, Del/T790M, Del/T790M/L718Q, and L858R/T790M/L718Q.

In one embodiment, the compounds of the present application are capable of modulating (e.g., inhibiting or decreasing) the activity of EGFR containing one or more mutations, but do not affect the activity of a wild-type EGFR.

Modulation of EGFR containing one or more mutations, such as those described herein, but not a wild-type EGFR, provides a novel approach to the treatment, prevention, or amelioration of diseases including, but not limited to, cancer and metastasis, inflammation, arthritis, systemic lupus erthematosus, skin-related disorders, pulmonary disorders, cardiovascular disease, ischemia, neurodegenerative disorders, liver disease, gastrointestinal disorders, viral and bacterial infections, central nervous system disorders, Alzheimer's disease, Parkinson's disease, Huntington's disease, amyotrophic lateral sclerosis, spinal cord injury, and peripheral neuropathy.

In one embodiment, the compounds of the application exhibit greater inhibition of EGFR containing one or more mutations as described herein relative to a wild-type EGFR. In certain embodiments, the compounds of the application exhibit at least 2-fold, 3-fold, 5-fold, 10-fold, 25-fold, 50-fold or 100-fold greater inhibition of EGFR containing one or more mutations as described herein relative to a wild-type EGFR. In various embodiments, the compounds of the application exhibit up to 1000-fold greater inhibition of EGFR containing one or more mutations as described herein relative to a wild-type EGFR. In various embodiments, the compounds of the application exhibit up to 10000-fold greater inhibition of EGFR having a combination of mutations selected from L858R/T790M, Del/T790M, Del/T790M/L718Q, and L858R/T790M/L718Q relative to a wild-type EGFR.

In various embodiments, the compounds of the application exhibit from about 2-fold to about 10-fold greater inhibition of EGFR containing one or more mutations as described herein relative to a wild-type EGFR. In various embodiments, the compounds of the application exhibit from about 10-fold to about 100-fold greater inhibition of EGFR containing one or more mutations as described herein relative to a wild-type EGFR. In various embodiments, the compounds of the application exhibit from about 100-fold to about 1000-fold greater inhibition of EGFR containing one or more mutations as described herein relative to a wild-type EGFR. In various embodiments, the compounds of the application exhibit from about 1000-fold to about 10000-fold greater inhibition of EGFR containing one or more mutations as described herein relative to a wild-type EGFR.

In certain embodiments, the compounds of the application exhibit at least 2-fold greater inhibition of EGFR having a combination of mutations selected from L858R/T790M, Del/T790M, Del/T790M/L718Q, and L858R/T790M/L718Q relative to a wild-type EGFR. In certain embodiments, the compounds of the application exhibit at least 3-fold greater inhibition of EGFR having a combination of mutations selected from L858R/T790M, Del/T790M, Del/T790M/L718Q, and L858R/T790M/L718Q relative to a wild-type EGFR. In certain embodiments, the compounds of the application exhibit at least 5-fold greater inhibition of EGFR having a combination of mutations selected from L858R/T790M, Del/T790M, Del/T790M/L718Q, and L858R/T790M/L718Q relative to a wild-type EGFR. In certain embodiments, the compounds of the application exhibit at least 10-fold greater inhibition of EGFR having a combination of mutations selected from L858R/T790M, Del/T790M, Del/T790M/L718Q, and L858R/T790M/

L718Q relative to a wild-type EGFR. In certain embodiments, the compounds of the application exhibit at least 25-fold greater inhibition of EGFR having a combination of mutations selected from L858R/T790M, Del/T790M, Del/T790M/L718Q, and L858R/T790M/L718Q relative to a wild-type EGFR. In certain embodiments, the compounds of the application exhibit at least 50-fold greater inhibition of EGFR having a combination of mutations selected from L858R/T790M, Del/T790M, Del/T790M/L718Q, and L858R/T790M/L718Q relative to a wild-type EGFR. In certain embodiments, the compounds of the application exhibit at least 100-fold greater inhibition of EGFR having a combination of mutations selected from L858R/T790M, Del/T790M, Del/T790M/L718Q, and L858R/T790M/L718Q relative to a wild-type EGFR.

In some embodiments, the inhibition of EGFR activity is measured by $IC_{50}$.

In some embodiments, the inhibition of EGFR activity is measured by $EC_{50}$.

In some embodiments, the compounds of the application covalently modify Cysteine 797 in EGFR.

In some embodiments, the application provides a compound comprising an irreversible kinase inhibitor, wherein the compound is a more potent inhibitor of a drug-resistant EGFR mutant relative to a wild type EGFR. For example, the compound can be at least about 2-fold, 3-fold, 5-fold, 10-fold, 25-fold, 50-fold or about 100-fold more potent at inhibiting the kinase activity of the drug-resistant EGFR mutant relative to a wild-type EGFR. In some embodiments, the drug-resistant EGFR mutant is resistant to one or more known EGFR inhibitors, including but not limited to gefitinib, erlotinib, lapatinib, WZ4002:

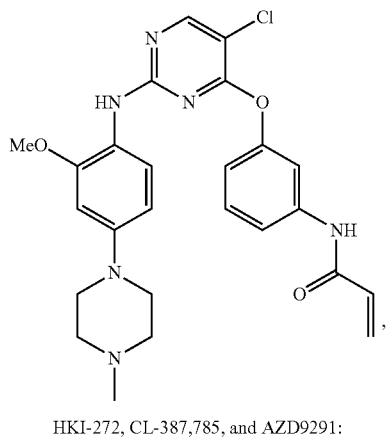

HKI-272, CL-387,785, and AZD9291:

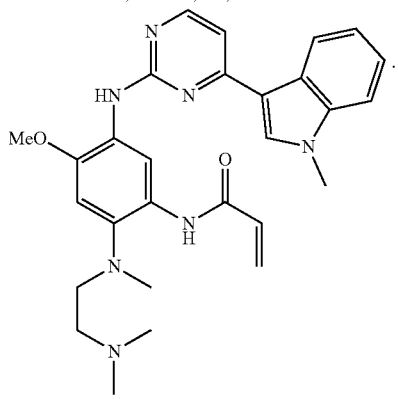

In some embodiments, the drug-resistant EGFR mutant comprises a sensitizing mutation, such as Del and L858R.

In some embodiments, the application provides a compound comprising an irreversible kinase inhibitor, wherein the compound inhibits kinase activity of a drug-resistant EGFR mutant harboring a sensitizing mutation (e.g., Del and L858R) and a drug-resistance mutation (e.g., T790M, L718Q, and L844V) with less than a 10-fold difference in potency (e.g., as measured by $IC_{50}$) relative to an EGFR mutant harboring the sensitizing mutation but not the drug-resistance mutation. In some embodiments, the difference in potency is less than about 9-fold, 8-fold, 7-fold, 6-fold, 5-fold, 4-fold, 3-fold, or 2-fold.

In some embodiments, the application provides a compound comprising an irreversible kinase inhibitor, wherein the compound is more potent than one or more known EGFR inhibitors, including but not limited to gefitinib, erlotinib, lapatinib, WZ4002, HKI-272, CL-387,785, and AZD9291, at inhibiting the activity of EGFR containing one or more mutations as described herein, such as T790M, L718Q, L844V, L858R, and Del. For example, the compound can be at least about 2-fold, 3-fold, 5-fold, 10-fold, 25-fold, 50-fold or about 100-fold more potent (e.g., as measured by $IC_{50}$) than gefitinib, erlotinib, lapatinib, WZ4002, HKI-272, CL-387,785, and AZD9291 at inhibiting the activity of the EGFR containing one or more mutations as described herein.

In some embodiments, the application provides a compound comprising an irreversible kinase inhibitor, wherein the compound is less potent than one or more known EGFR inhibitors, including but not limited to gefitinib, erlotinib, lapatinib, WZ4002, HKI -272, CL-387,785, and AZD9291, at inhibiting the activity of a wild-type EGFR. For example, the compound can be at least about 2-fold, 3-fold, 5-fold, 10-fold, 25-fold, 50-fold or about 100-fold less potent (e.g., as measured by $IC_{50}$) than gefitinib, erlotinib, lapatinib, WZ4002, HKI-272, CL-387,785, and AZD9291, at inhibiting the activity of a wild-type EGFR.

Potency of the inhibitor can be determined by $IC_{50}$ value. A compound with a lower $IC_{50}$ value, as determined under substantially similar conditions, is a more potent inhibitor relative to a compound with a higher $IC_{50}$ value. In some embodiments, the substantially similar conditions comprise determining an EGFR-dependent phosphorylation level in 3T3 cells expressing a wild type EGFR, a mutant EGFR, or a fragment of any thereof.

An EGFR sensitizing mutation comprises without limitation L858R, G719S, G719C, G719A, L861Q, a deletion in exon 19 and/or an insertion in exon 20. A drug-resistant EGFR mutants can have without limitation a drug resistance mutation comprising T790M, T854A, L718Q or D761Y.

The selectivity between wild-type EGFR and EGFR containing one or more mutations as described herein can also be measured using cellular proliferation assays where cell proliferation is completely dependent on kinase activity. For example, murine Ba/F3 cells transfected with a suitable version of wild-type EGFR (such as VIII; containing a WT EGFR kinase domain), or Ba/F3 cells transfected with L858R/T790M, Del/T790M/L718Q, L858R/T790M/L718Q or Exon 19 deletion/T790M can be used. Proliferation assays are performed at a range of inhibitor concentrations (10 μM, 3 μM, 1.1 μM, 330 nM, 110 nM, 33 nM, 11 nM, 3 nM, 1 nM) and an $EC_{50}$ is calculated.

An alternative method to measure effects on EGFR activity is to assay EGFR phosphorylation. Wild type or mutant (L858R/T790M, Del/T790M, Del/T790M/L718Q, or L858R/T790M/L718Q) EGFR can be transfected into NIH- 3T3 cells (which do not normally express endogenous EGFR) and the ability of the inhibitor (using concentrations as above) to inhibit EGFR phosphorylation can be assayed. Cells are exposed to increasing concentrations of inhibitor for 6 hours and stimulated with EGF for 10 minutes. The effects on EGFR phosphorylation are assayed by Western Blotting using phospho-specific (Y1068) EGFR antibodies.

In another aspect, the present application relates to a compound that covalently modifies Cysteine 797 in EGFR, wherein the compound exhibits greater than 2-fold, 3-fold, 5-fold, 10-fold, 25-fold, 50-fold, 100-fold, or 1000-fold inhibition of EGFR containing one or more mutations as described herein (e.g., L858R/T790M, Del/T790M, Del/T790M/L718Q, or L858R/T790M/L718Q) relative to a wild-type EGFR.

Definitions

Listed below are definitions of various terms used to describe this application. These definitions apply to the terms as they are used throughout this specification and claims, unless otherwise limited in specific instances, either individually or as part of a larger group.

The term "alkyl," as used herein, refers to saturated, straight- or branched-chain hydrocarbon radicals containing, in certain embodiments, between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "alkoxy" refers to an —O-alkyl radical.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound. Examples of $C_3$-$C_8$-cycloalkyl include, but not limited to, cyclopropyl, cyclobutyl, cyclopentyl, cyclohexyl, cycloheptyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2] octyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue attached to a heteroaryl ring. Examples include, but are not limited to, pyridinylmethyl, pyrimidinylethyl and the like.

The term "heterocyclyl," or "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (v) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl) where $C_1$-$C_{12}$ alkyl is as previously defined.

The term "dialkylamino" refers to a group having the structure —N($C_1$-$C_{12}$ alkyl)$_2$ where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the application, any of the aryls, substituted aryls, heteroaryls and substituted heteroaryls described herein, can be any aromatic group. Aromatic groups can be substituted or unsubstituted.

The terms "hal," "halo," and "halogen," as used herein, refer to an atom selected from fluorine, chlorine, bromine and iodine.

As described herein, compounds of the application may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I, —OH, protected hydroxy, —NO$_2$, —CN, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)— heteroaryl, —C(O)-heterocycloalkyl, —CONH$_2$, —CONH— C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)— heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$-heterocycloalkyl, NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, NHC(O)NH-heterocycloalkyl, NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl-SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

It is understood that the aryls, heteroaryls, alkyls, and the like can be further substituted.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "EGFR" herein refers to epidermal growth factor receptor kinase.

The term "HER" or "Her", herein refers to human epidermal growth factor receptor kinase.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating" and "treatment" refer to a method of alleviating or abating a disease and/or its attendant symptoms.

As used herein, "preventing" or "prevent" describes reducing or eliminating the onset of the symptoms or complications of the disease, condition or disorder.

As used herein, the term "pharmaceutically acceptable salt" refers to those salts of the compounds formed by the process of the present application which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the application, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present application which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present application which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present application. "Prodrug", as used herein means a compound which is convertible in vivo by metabolic means (e.g., by hydrolysis) to afford any compound delineated by the formulae of the instant application. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This application also encompasses pharmaceutical compositions containing, and methods of treating disorders through administering, pharmaceutically acceptable prodrugs of compounds of the application. For example, compounds of the application having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the application. The amino acid residues include but are not limited to the 20 naturally occurring amino acids commonly designated by three letter symbols and also includes 4-hydroxyproline, hydroxyysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities Combinations of substituents and variables envisioned by this application are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The application also provides for a pharmaceutical composition comprising a compound of Formula (I), or a pharmaceutically acceptable ester, salt, or prodrug thereof, together with a pharmaceutically acceptable carrier.

In another aspect, the application provides a kit comprising a compound capable of inhibiting EGFR activity selected from one or more compounds of Formula (I), or a pharmaceutically acceptable salt, hydrate, solvate, prodrug, stereoisomer, or tautomer thereof, and instructions for use in treating cancer.

In another aspect, the application provides a method of synthesizing a compound of Formula (I).

The synthesis of the compounds of the application can be found herein and in the Examples below.

Another embodiment is a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^3$H, $^2$H, $^{14}$C, $^{13}$C, $^{18}$F, $^{35}$S, $^{32}$P, $^{125}$I, and $^{131}$I) introduced into the compound. Such compounds are useful for drug metabolism studies and diagnostics, as well as therapeutic applications.

A compound of the application can be prepared as a pharmaceutically acceptable acid addition salt by reacting the free base form of the compound with a pharmaceutically acceptable inorganic or organic acid. Alternatively, a pharmaceutically acceptable base addition salt of a compound of the application can be prepared by reacting the free acid form of the compound with a pharmaceutically acceptable inorganic or organic base.

Alternatively, the salt forms of the compounds of the application can be prepared using salts of the starting materials or intermediates.

The free acid or free base forms of the compounds of the application can be prepared from the corresponding base addition salt or acid addition salt from, respectively. For example a compound of the application in an acid addition salt form can be converted to the corresponding free base by treating with a suitable base (e.g., ammonium hydroxide solution, sodium hydroxide, and the like). A compound of the application in a base addition salt form can be converted to the corresponding free acid by treating with a suitable acid (e.g., hydrochloric acid, etc.).

Prodrug derivatives of the compounds of the application can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the application with a suitable carbamylating agent (e.g., 1,1-acyloxyalkylcarbanochloridate, para-nitrophenyl carbonate, or the like).

Protected derivatives of the compounds of the application can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present application can be conveniently prepared, or formed during the process of the application, as solvates (e.g., hydrates). Hydrates of compounds of the present application can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In addition, some of the compounds of this application have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present application. Optical isomers may be prepared from their respective optically active precursors by the procedures described herein, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). The compounds of this application may also be represented in multiple tautomeric forms, in such instances, the application expressly includes all tautomeric forms of the compounds described herein (e.g., alkylation of a ring system may result in alkylation at multiple sites, the application expressly includes all such reaction products). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present application. All crystal forms of the compounds described herein are expressly included in the present application.

In the present specification, the structural formula of the compound represents a certain isomer for convenience in some cases, but the present application includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present application. Furthermore, so-called metabolite which is produced by degradation of the present compound in vivo is included in the scope of the present application.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present application, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

It is to be understood that the compounds of the present application may be depicted as different tautomers. It should also be understood that when compounds have tautomeric forms, all tautomeric forms are intended to be included in the scope of the present application, and the naming of the compounds does not exclude any tautomer form.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present application. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of this application may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the application are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Method of Synthesizing the Compounds

The compounds of the present application may be made by a variety of methods, including standard chemistry. The synthetic processes of the application can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester or prodrug thereof. Suitable synthetic routes are depicted in the Scheme I below.

Compounds of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; and Greene, T. W., Wuts, P. G. M., *Protective Groups in Organic Synthesis*, 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present application.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

All the abbreviations used in this application are found in "Protective Groups in Organic Synthesis" by John Wiley & Sons, Inc, or the MERCK INDEX by MERCK & Co., Inc, or other chemistry books or chemicals catalogs by chemicals vendor such as Aldrich, or according to usage know in the art.

The compounds of the present application can be prepared in a number of ways well known to those skilled in the art of organic synthesis. By way of example, compounds of the present application can be synthesized using the methods described below, together with synthetic methods known in the art of synthetic organic chemistry, or variations thereon as appreciated by those skilled in the art. Preferred methods include but are not limited to those methods described below. Compounds of the present application can be synthesized by following the steps outlined in General Schemes 1 and 2 which comprise different sequences of assembling intermediates Ia, Ib, Ic, Id, Ie, If, Ig, Ih, Ii, Ij, Ik, Il, and Im. Starting materials are either commercially available or made by known procedures in the reported literature or as illustrated.

General Scheme 1

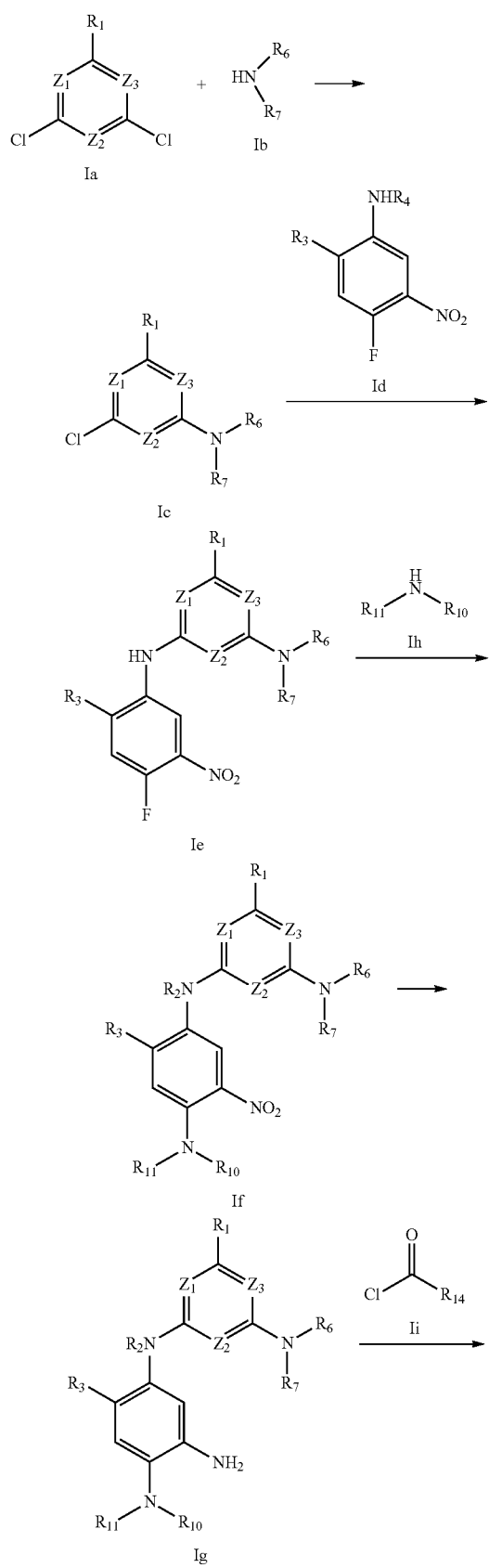

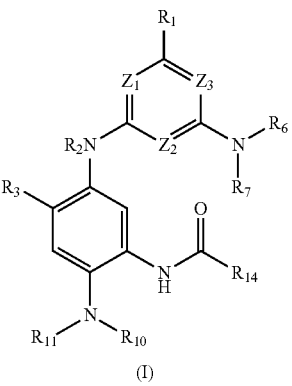

wherein $R_1$-$R_3$, $R_6$, $R_7$, $R_{10}$, $R_{11}$, $Z_1$, $Z_2$, and $Z_3$ are defined as in Formula (I).

The general way of preparing target molecules I by using intermediates Ia, Ib, Ic, Id, Ie, Ih, Ii, and Ig is outlined in General Scheme 1. Nucleophilic addition of amine Ib to Ia using a base, i.e., sodium hydride (NaH) or potassium hydride (KH), in solvent, i.e., DMF, at low temperatures provides intermediate Ic. Intermediate Ie is then prepared by nucleophilic addition of aryl amine Id to intermediate Ic in the presence of an acid, i.e., trifluoroacetic acid and in a solvent, i.e., 2-butanol, at elevated temperature. Nucleophilic addition of amine Ih to intermediate Ie using a base, i.e., triethylamine or N,N-diisopropylethylamine (DIPEA), in solvent, i.e., dimethylformamide (DMF), at elevated temperatures provides intermediate If. Reduction of the nitro group in the presence of a metal salt, i.e., stannous chloride ($SnCl_2$) or chromium (II) chloride ($CrCl_2$), and an acid, i.e., hydrochloric acid (HCl) in solvent, i.e., ethyl acetate. Acylation of Ig with acyl chloride Ii using a base, i.e., sodium bicarbonate ($NaHCO_3$) or potassium bicarbonate ($KHCO_3$), in solvent, i.e., tetrahydrofuran/water ($THF/H_2O$) provides the desired compound of Formula (I).

General Scheme 2

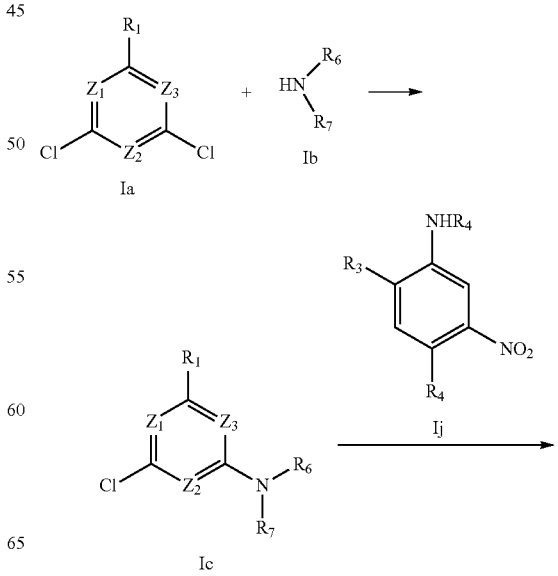

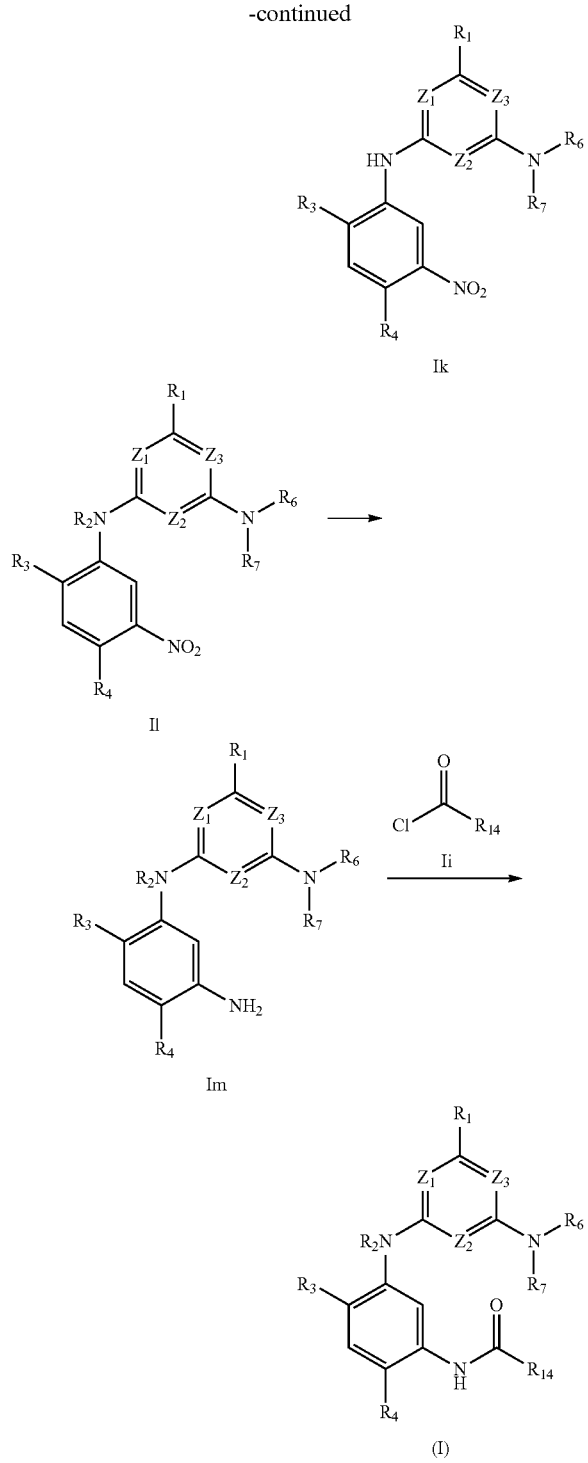

wherein $R_1$-$R_4$, $R_6$, $R_7$, $R_{10}$, $R_{11}$, $Z_1$, $Z_2$, and $Z_3$ are defined as in Formula (I).

The general way of preparing target molecules I by using intermediates Ia, Ib, Ic, Id, Ii, Ij, Ik, Il, Im and Ig is outlined in General Scheme 2. Nucleophilic addition of amine Ib to Ia using a base, i.e., sodium hydride (NaH) or potassium hydride (KH), in solvent, i.e., DMF, at low temperatures provides intermediate Ic. Intermediate Ik is then prepared by nucleophilic addition of aryl amine Ij to intermediate Ic in the presence of an acid, i.e., trifluoroacetic acid and in a solvent, i.e., 2-butanol, at elevated temperature. Reduction of the nitro group in the presence of a metal salt, i.e., stannous chloride (SnCl) or chromium (II) chloride ($CrCl_2$), and an acid, i.e., hydrochloric acid (HCl), in solvent, i.e., ethyl acetate provides intermediate Im. Acylation of Im with acyl chloride Ii using a base, i.e., sodium bicarbonate ($NaHCO_3$) or potassium bicarbonate ($KHCO_3$), in solvent, i.e., tetrahydrofuran/water ($THF/H_2O$) provides the desired compound of Formula (I).

A mixture of enantiomers, diastereomers, cis/trans isomers resulting from the process described above can be separated into their single components by chiral salt technique, chromatography using normal phase, reverse phase or chiral column, depending on the nature of the separation.

It should be understood that in the description and formula shown above, the various groups $R_1$-$R_4$, $R_6$, $R_7$, $R_{10}$, $R_{11}$, $Z_1$, $Z_2$, and $Z_3$ and other variables are as defined above, except where otherwise indicated. Furthermore, for synthetic purposes, the compounds of General Schemes 1 and 2 are mere representatives with elected radicals to illustrate the general synthetic methodology of the compounds of Formula (I) as defined herein.

Biological Assays

Cell Proliferation Assays and Growth Assays

Murine Ba/F3 cells are engineered to express mutant EGFR protein along with untransformed Ba/F3 cells and are used to performed single drug screens. Cell viability is assessed after 72 hours of compound i.e., compounds of Formula (I), exposure using the colorimetric cell proliferation MTS assay kit (Promega).

The selectivity between wild-type EGFR and the L858R/T790M or Exon 19 Deletion/T790M EGFR mutants is measured using cellular proliferation assays where cell proliferation is completely dependent on kinase activity. For example, murine Ba/F3 cells transfected with a suitable version of wild-type EGFR (such as VIII; containing a WT EGFR kinase domain), or Ba/F3 cells transfected with L858R/T790M or Exon 19 deletion/T790M are used. Proliferation assays are performed at a range of inhibitor concentrations and an $EC_{50}$ is calculated.

An alternative method to measure effects on EGFR activity is to assay EGFR phosphorylation. Wild type or mutant (L858R/T790M or Del19/T790M) EGFR is transfected into NIH-3T3 cells (which do not normally express endogenous EGFR) and the ability of the inhibitor to inhibit EGFR phosphorylation is assayed. Cells are exposed to increasing concentrations of inhibitor and then stimulated with EGF. The effects on EGFR phosphorylation are assayed by Western Blotting using phospho-specific (Y1068) EGFR antibodies.

Antibodies and Western Blotting

Cells are and lysed in buffer. Western blot analyses are conducted after separation by SDS/PAGE electrophoresis and transfer to polyvinylidene difluoride-P membrane. Immunoblotting is then performed. Antibody binding is detected using an enhanced chemiluminescence system.

Pepsin Digestion and Peptide Analysis

For the elucidation of the modification site, all of the proteins are digested offline with pepsin in an enzyme:substrate ratio of 1:1. The pepsin digestion is performed in a buffer having a pH 2.5. The reaction is then carried out on ice. The resulting peptides are injected into a UPLC system, trapped and desalted for 3 min at 100 μL/min and then separated. Identification of the peptic fragments is accomplished through a combination of exact mass analysis and $MS^{E12}$ Generation of Mouse Cohorts and Treatment with Compounds of Formula (I)

EGFR-TL (T790M/L858R) and EGFR exon 19 Deletion-T790M (TD) inducible bitransgenic mice are generated and characterized. Briefly, exon 19 deletion is introduced in the human EGFR gene through site directed mutagenesis in the pTRE2-hyg-EGFR-T790M. The constructs were then digested to release the entire allele. Transgenic mice are then generated by injection of the construct into FVB/N fertilized eggs. Progeny are genotyped through PCR. Founders are crossed with CCSP-rtTA mice and inducible bitransgenic mice with high and inducible expression of the mutant hEGFR transgene are identified and expanded for subsequent analyses and experiments.

Cohorts of EGFR TL/CCSP-rtTA and EGFR TD/CCSP-rtTA are put on doxycycline diet at 5 weeks of age to induce the expression of mutant EGFR. These mice undergo MRI after 6 to 8 weeks of doxycycline diet to document and quantify the lung cancer burden before being assigned to various treatment study cohorts. Mice are then treated either with vehicle (NMP (10% 1-methyl-2-pyrrolidinone: 90% PEG-300) alone or a compound of Formula (I) daily. After 2 weeks of treatment, these mice undergo a second round of MRI to document their response to the treatment.

MRI Scanning and Tumor Volume Measurement

Mice are anesthetized with isoflurane in an oxygen/air mixture. The respiratory and cardiac rates of anesthetized mice are monitored. The animals are then imaged with a rapid acquisition with relaxation enhancement (RARE) sequence and with a gradient echo fast imaging (GEFI) sequence Immunohistochemical Analyses Immunohistochemistry is performed on formal fixed paraffin embedded tumor sections. The antibodies used are: total EGFR and phospho-EGFR Y1068 and Ki67. Apoptosis is measured by counting nuclear bodies in H&E (Hematoxylin and eosin) stained sections and by a terminal deoxynucleotidyl-transferase mediated dUTP-biotin nick end labeling (TUNEL) assay.

Pharmacokinetic Analyses

Dose administration: All mice are weighed before dose administration and randomized. For intravenous administration, a freshly prepared solution of a compound of Formula (I) is administered via tail vein at a slow and steady rate. For oral administration, freshly prepared suspension of a compound of Formula (I) is administered by stomach intubation using an oral feeding needle.

Blood samples are collected from the saphenous vein of each mouse at regular intervals. During each sampling point, blood samples are collected in labeled microtubes containing K2EDTA as an anticoagulant. Samples are centrifuged and the recovered quantity of plasma from each sample is transferred to labeled micro-tubes. The plasma samples are then stored at a low temperature until bioanalysis.

Bioanalytical method for the determination of a compound of Formula (I) in mouse plasma is developed using LC-MS/MS equipment. The method is partially validated prior to sample analysis.

The pharmacokinetic parameters of a compound of Formula (I) such as $T_{max}$, $C_{max}$, AUC, CL, $V_d$, $T_{1/2}$, and bioavailability in mouse plasma are determined from the concentration-time data using non-compartmental analysis.

Serum Creatinine and White Blood Cell Count Analyses

Blood is collected from vehicle and compound of Formula (I) treated mice into appropriate tubes and analyzed.

Methods of the Application

In another aspect, the application provides a method of inhibiting a kinase, comprising contacting the kinase with a compound of Formula (I), or a pharmaceutically acceptable salt, hydrate, solvate, prodrug, stereoisomer, or tautomer thereof. In one embodiment, the kinase comprises a cysteine residue. In a further embodiment, the cysteine residue is located in or near the position equivalent to Cys 797 in EGFR, including such position in Jak3, Blk, Bmx, Btk, HER2 (ErbB2), HER4 (ErbB4), Itk, Tec, and Txk.

In another aspect, the application provides a method of inhibiting a kinase, the method comprising administering to a subject in need thereof an effective amount of a compound of Formula (I), or a pharmaceutically acceptable salt, hydrate, solvate, prodrug, stereoisomer, or tautomer thereof. In one embodiment, the EGFR is a Her-kinase.

In still another aspect, the application provides a method of inhibiting epidermal growth factor receptor (EGFR), the method comprising administering to a subject in need thereof an effective amount of a compound of Formula (I), or a pharmaceutically acceptable salt, hydrate, solvate, prodrug, stereoisomer, or tautomer thereof.

Another aspect of the application provides a method of treating or preventing a disease, the method comprising administering to a subject in need thereof an effective amount of a compound of Formula (I), or a pharmaceutically acceptable salt, hydrate, solvate, prodrug, stereoisomer, or tautomer thereof. In one embodiment, the disease is mediated by a kinase. In a further embodiment, the kinase comprises a cysteine residue. In still a further embodiment, the cysteine residue is located in or near the position equivalent to Cys 797 in EGFR, including such positions in Jak3, Blk, Bmx, Btk, HER2 (ErbB2), HER4 (ErbB4), Itk, Tec, and Txk.

In other embodiments, the disease is mediated by EGFR (e.g., EGFR plays a role in the initiation or development of the disease). In a further embodiment, the EGFR is a Her-kinase. In a further embodiment, the Her-kinase is HER1, HER2, or HER4.

In certain embodiments, the disease is cancer or a proliferation disease.

In a further embodiment, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In other embodiments, the disease is inflammation, arthritis, rheumatoid arthritis, spondyiarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamus cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, and peripheral neuropathy, or B-Cell Lymphoma.

In a further embodiment, the disease is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, dermatitis, pain, pulmonary disorders, lung inflammation, adult respiratory distress syndrome, pulmonary sarcoisosis, asthma, chronic pulmonary inflammatory disease, and chronic obstructive pulmonary disease (COPD), cardiovascular disease, arteriosclerosis, myocardial infarction (including post-myocardial infarction indications), congestive heart failure, cardiac reperfusion injury, inflammatory bowel disease, Crohn's disease, gastritis, irritable bowel syndrome, leukemia or lymphoma.

In another aspect, the application provides a method of treating a kinase mediated disorder, the method comprising administering to a subject in need thereof an effective amount of a compound of Formula (I), or a pharmaceutically acceptable salt, hydrate, solvate, prodrug, stereoisomer, or tautomer thereof. In one embodiment, the compound is an inhibitor of HER1, HER2, or HER4. In another embodiment, the subject is administered an additional therapeutic agent. In other embodiments, the compound and the additional therapeutic agent are administered simultaneously or sequentially.

In another embodiment, the disease is cancer. In a further embodiment, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In another aspect, the application provides a method of treating or preventing cancer, wherein the cancer cell comprise activated EGFR, comprising administering to a subject in need thereof an effective amount of a compound of Formula (I), or a pharmaceutically acceptable salt, hydrate, solvate, prodrug, stereoisomer, or tautomer thereof.

In certain embodiments, the EGFR activation is selected from mutation of EGFR, amplification of EGFR, expression of EGFR, and ligand mediated activation of EGFR.

In further embodiment, the mutation of EGFR is located at G719S, G719C, G719A, L858R, L861Q, an exon 19 deletion mutation or an exon 20 insertion mutation.

Another aspect of the application provides a method of treating or preventing cancer in a subject, wherein the subject is identified as being in need of EGFR inhibition for the treatment of cancer, comprising administering to the subject an effective amount of a compound of Formula (I), or a pharmaceutically acceptable salt, hydrate, solvate, prodrug, stereoisomer, or tautomer thereof.

In certain embodiments, the subject is identified as being in need of EGFR inhibition is resistant to a known EGFR inhibitor, including but not limited to, gefitinib or erlotinib. In certain embodiments, a diagnostic test is performed to determine if the subject has an activating mutation in EGFR. In certain embodiments, a diagnostic test is performed to determine if the subject has an EGFR harboring an activating and a drug resistance mutation. Activating mutations comprise without limitation L858R, G719S, G719C, G719A, L718Q, L861Q, a deletion in exon 19 and/or an insertion in exon 20. Drug resistant EGFR mutants can have without limitation a drug resistance mutation comprising T790M, T854A, L718Q, or D761Y. The diagnostic test can comprise sequencing, pyrosequencing, PCR, RT-PCR, or similar analysis techniques known to those of skill in the art that can detect nucleotide sequences.

In another aspect, the application provides a method of treating or preventing cancer, wherein the cancer cell comprises an activated ERBB2, comprising administering to a subject in need thereof an effective amount of a compound of Formula (I), or a pharmaceutically acceptable salt, hydrate, solvate, prodrug, stereoisomer, or tautomer thereof. In certain embodiments, the ERBB2 activation is selected from mutation of ERBB2, expression of ERBB2 and amplification of ERBB2. In a further embodiment, the mutation is a mutation in exon 20 of ERBB2.

In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In still another aspect, the application provides a method of treating cancer in a subject, wherein the subject is identified as being in need of ERBB2 inhibition for the treatment of cancer, comprising administering to the subject in need thereof an effective amount of a compound of Formula (I), or a pharmaceutically acceptable salt, hydrate, solvate, prodrug, stereoisomer, or tautomer thereof.

Another aspect of the application provides a method of preventing resistance to a known EGFR inhibitor, including but not limited to, gefitinib or erlotinib in a disease, comprising administering to a subject in need thereof an effective amount of a compound of Formula (I), or a pharmaceutically acceptable salt, hydrate, solvate, prodrug, stereoisomer, or tautomer thereof.

In certain embodiments, the disease is cancer. In a further embodiment, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In certain embodiments, the application provides a method of treating any of the disorders described herein, wherein the subject is a human. In certain embodiments, the application provides a method of preventing any of the disorders described herein, wherein the subject is a human.

In another aspect, the application provides a compound of Formula (I), or a pharmaceutically acceptable salt, hydrate, solvate, prodrug, stereoisomer, or tautomer thereof, for use in the manufacture of a medicament for treating or preventing a disease in which EGFR plays a role.

In still another aspect, the application provides the use of a compound of Formula (I), or a pharmaceutically acceptable salt, hydrate, solvate, prodrug, stereoisomer, or tautomer thereof, in the treatment or prevention of a disease in which EGFR plays a role.

As inhibitors of Her kinases, the compounds and compositions of this application are particularly useful for treating or lessening the severity of a disease, condition, or disorder where a protein kinase is implicated in the disease, condition, or disorder. In one aspect, the present application provides a method for treating or lessening the severity of a disease, condition, or disorder where a protein kinase is implicated in the disease state. In another aspect, the present application provides a method for treating or lessening the severity of a kinase disease, condition, or disorder where inhibition of enzymatic activity is implicated in the treatment of the disease. In another aspect, this application provides a method for treating or lessening the severity of a disease, condition, or disorder with compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor.

In some embodiments, said method is used to treat or prevent a condition selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

One aspect of this application provides compounds that are useful for the treatment of diseases, disorders, and conditions characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colonrectum, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral Tcell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the application, the present application provides for the use of one or more compounds of the application in the manufacture of a medicament for the treatment of cancer, including without limitation the various types of cancer disclosed herein.

In some embodiments, the compounds of this application are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the compounds of this application are useful for treating hematopoietic disorders, in particular, acute-myelogenous leukemia (AML), chronic-myelogenous leukemia (CML), acute-promyelocytic leukemia, and acute lymphocytic leukemia (ALL).

This application further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intraepithelial tissue.

Examples of neurodegenerative diseases include, without limitation, Adrenoleukodystrophy (ALD), Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, and Toxic encephalopathy.

Another aspect of this application provides a method for the treatment or lessening the severity of a disease selected from a proliferative or hyperproliferative disease, or a neurodegenerative disease, comprising administering an effective amount of a compound, or a pharmaceutically acceptable composition comprising a compound, to a subject in need thereof.

As inhibitors of Her kinases, the compounds and compositions of this application are also useful in biological samples. One aspect of the application relates to inhibiting protein kinase activity in a biological sample, which method comprises contacting said biological sample with a compound of the application or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this application relates to the study of Her kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as Her kinase inhibitors may be assayed in vitro, in vivo, or in a cell line. In vitro assays include assays that determine inhibition of either the kinase activity or ATPase activity of the activated kinase. Alternate in vitro assays quantitate the ability of the inhibitor to bind to the protein kinase and may be measured either by radio labelling the inhibitor prior to binding, isolating the inhibitor/kinase complex and determining the amount of radio label bound, or by running a competition experiment where new inhibitors are incubated with the kinase bound to known radioligands. Detailed conditions for assaying a compound utilized in this application as an inhibitor of various kinases are set forth in the Examples below.

In accordance with the foregoing, the present application further provides a method for preventing or treating any of the diseases or disorders described above in a subject in need of such treatment, which method comprises administering to said subject a therapeutically effective amount of a compound of the application, or a pharmaceutically acceptable salt, hydrate, solvate, prodrug, stereoisomer, or tautomer thereof. For any of the above uses, the required dosage will vary depending on the mode of administration, the particular condition to be treated and the effect desired.

Pharmaceutical Compositions

In another aspect, the application provides a pharmaceutical composition comprising a compound of Formula I, or a pharmaceutically acceptable ester, salt, or prodrug thereof, together with a pharmaceutically acceptable carrier.

Compounds of the application can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present application in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present application with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the application can be administered in therapeutically effective amounts in a combinational therapy with one or more therapeutic agents (pharmaceutical combinations) or modalities, e.g., non-drug therapies. For example, synergistic effects can occur with other antiproliferative, anti-cancer, immunomodulatory or anti-inflammatory substances. Where the compounds of the application are administered in conjunction with other therapies, dosages of the co-administered compounds will of course vary depending on the type of co-drug employed, on the specific drug employed, on the condition being treated and so forth.

Combination therapy includes the administration of the subject compounds in further combination with other biologically active ingredients (such as, but not limited to, a second and different antineoplastic agent) and non-drug therapies (such as, but not limited to, surgery or radiation treatment). For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

In one aspect of the application, the compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g., MET, RON, SEA, SEX); insulin receptor (e.g. IGFI-R); Eph (e.g. CEK5, CEK8, EBK, ECK, EEK, EHK-1, EHK-2, ELK, EPH, ERK, HEK, MDK2, MDK5, SEK); Axl (e.g., Mer/Nyk, Rse); RET; and platelet-derived growth factor receptor (PDGFR) (e.g., PDGF.alpha.-R, PDG.beta.-R, CSFI-RIFMS, SCF-R/C-KIT, VEGF-R/FLT, NEK/FLK 1, FLT3/FLK2/STK-1). Non-receptor tyrosine kinase families include, but are not limited to, BCR-ABL (e.g., p43.sup.abl, ARG); BTK (e.g. TTK/EMT, TEC); CSK, FAK, FPS, JAK, SRC, BMX, FER, CDK and SYK.

In another aspect of the application, the subject compounds may be administered in combination with one or more agents that modulate non-kinase biological targets or processes. Such targets include histone deacetylases (HDAC), DNA methyltransferase (DNMT), heat shock proteins (e.g. HSP90), and proteosomes.

In a preferred embodiment, subject compounds may be combined with antineoplastic agents (e.g., small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafinib, CNF2024, RG108, BMS387032, Affinitak, Avastin, Herceptin, Erbitux, AG24322, PD325901, ZD6474, PD184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the application are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cyclophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); antitumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA)).

In certain preferred embodiments, the compounds of the application are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the application, the subject compounds are administered in combination with radiation therapy. Radiation is commonly delivered internally (implantation of radioactive material near cancer site) or externally (from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the application can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that the compounds of the application may advantageously be used in conjunction with one or more adjunctive therapeutic agents. Examples of suitable agents for adjunctive therapy include a $5HT_1$ agonist, such as a triptan (e.g., sumatriptan or naratriptan); an adenosine A1 agonist; an EP ligand; an NMDA modulator, such as a glycine antagonist; a sodium channel blocker (e.g. lamotrigine); a substance P antagonist (e.g., an NKi antagonist); a cannabinoid; acetaminophen or phenacetin; a 5-lipoxygenase inhibitor; a leukotriene receptor antagonist; a DMARD (e.g., methotrexate); gabapentin and related compounds; a tricyclic antidepressant (e.g., amitryptilline); a neurone stabilising antiepileptic drug; a mono-aminergic uptake inhibitor (e.g., venlafaxine); a matrix metalloproteinase inhibitor; a nitric oxide synthase (NOS) inhibitor, such as an iNOS or an nNOS inhibitor; an inhibitor of the release, or action, of tumor necrosis factor a; an antibody therapy, such as a monoclonal antibody therapy; an antiviral agent, such as a nucleoside inhibitor (e.g., lamivudine) or an immune system modulator (e.g., interferon); an opioid analgesic; a local anesthetic; a stimulant, including caffeine; an $H_2$-antagonist (e.g., ranitidine); a proton pump inhibitor (e.g., omeprazole); an antacid (e.g., aluminum or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g., codeine, hydrocodone, carmiphen, carbetapentane, or dextramethorphan); a diuretic; or a sedating or non-sedating antihistamine.

The pharmaceutical compositions of the present application comprise a therapeutically effective amount of a compound of the present application formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this application can be administered to humans and other animals orally, rectally, parenterally, intracistemally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present application, disorders are treated or prevented in a subject, such as a human or other animal, by administering to the subject a therapeutically effective amount of a compound of the application, in such amounts and for such time as is necessary to achieve the desired result. The term "therapeutically effective amount" of a compound of the application, as used herein, means a sufficient amount of the compound so as to decrease the symptoms of a disorder in a subject. As is well understood in the medical arts a therapeutically effective amount of a compound of this application will be at a reasonable benefit/risk ratio applicable to any medical treatment.

In general, compounds of the application will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 100 mg, conveniently administered, e.g., in divided doses up to four times a day or in retard form. Suitable unit dosage forms for oral administration comprise from ca. 1 to 50 mg active ingredient.

In certain embodiments, a therapeutic amount or dose of the compounds of the present application may range from about 0.1 mg/Kg to about 500 mg/Kg, alternatively from about 1 to about 50 mg/Kg. In general, treatment regimens according to the present application comprise administration to a patient in need of such treatment from about 10 mg to about 1000 mg of the compound(s) of this application per day in single or multiple doses. Therapeutic amounts or doses will also vary depending on route of administration, as well as the possibility of co-usage with other agents.

Upon improvement of a subject's condition, a maintenance dose of a compound, composition or combination of this application may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The application also provides for a pharmaceutical combinations, e.g., a kit, comprising a) a first agent which is a compound of the application as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g., a compound of the application and a co-agent, are both administered to a patient simultaneously in the form of a single entity or dosage. The term "non-fixed combination" means that the active ingredients, e.g. a compound of the application and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

In certain embodiments, these compositions optionally further comprise one or more additional therapeutic agents. For example, chemotherapeutic agents or other antiproliferative agents may be combined with the compounds of this application to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the compounds of this application may also be combined with include, without limitation: treatments for Alzheimer's Disease such as Ariceptl8 and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and antiparkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, antileukemic agents, and growth factors; and agents for treating immunodeficiency disorders such as gamma globulin.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are another embodiment of the present application.

In another aspect, the application provides a kit comprising a compound capable of inhibiting kinase activity selected from one or more compounds of Formula I, or pharmaceutically acceptable salts, hydrates, solvates, prodrugs, stereoisomers, or tautomers thereof, and instructions for use in treating cancer. In certain embodiments, the kit further comprises components for performing a test to determine whether a subject has activating and/or drug resistance mutations in EGFR.

In another aspect, the application provides a kit comprising a compound capable of inhibiting EGFR activity selected from a compound of Formula (I), or a pharmaceutically acceptable salt, hydrate, solvate, prodrug, stereoisomer, or tautomer thereof.

The application is further illustrated by the following examples and synthesis schemes, which are not to be construed as limiting this application in scope or spirit to the specific procedures herein described. It is to be understood that the examples are provided to illustrate certain embodiments and that no limitation to the scope of the application is intended thereby. It is to be further understood that resort may be had to various other embodiments, modifications, and equivalents thereof which may suggest themselves to those skilled in the art without departing from the spirit of the present application and/or scope of the appended claims.

EXAMPLES

Analytical Methods, Materials, and Instrumentation

All reactions were monitored by Waters LC/MS system (Waters 2489 UV/Visible Detector, Waters 3100 Mass, Waters 515 HPLC pump, Waters 2545 Binary Gradient Module, Waters Reagent Manager and Waters 2767 Sample Manager) using SunFire™ C18 column (4.6×50 mm, 5 µm particle size): solvent gradient=75% A at 0 min, 1% A at 5 min; solvent A=0.035% TFA in Water; solvent B=0.035% TFA in MeOH; flow rate: 1.8 mL/min and thin layer chromatography (TLC) with 0.25 mm E. Merck pre-coated silica gel plates (60 F254). Reaction products were purified by flash column chromatography using CombiFlash® Rf with Teledyne Isco RediSep® Rf High Performance Gold or Silicycle SiliaSep™ High Performance columns (4 g, 12 g, 24 g, 40 g, or 80 g) and Waters LC/MS system using SunFire™ Prep C18 column (19×50 mm, 5 µm particle size): solvent gradient=80% A at 0 min, 10% A at 8 min; solvent A=0.035% TFA in Water; solvent B=0.035% TFA in MeOH; flow rate: 25 mL/min. The purity of all compounds was over 95% and was analyzed with Waters LC/MS system. $^1$H NMR was obtained using a 600 MHz Varian Inova-600 and $^{13}$C NMR spectra was obtained using a 125 MHz Varian Inova-600 spectrometer. Chemical shifts are reported relative to chloroform (δ=7.24) or dimethyl sulfoxide (δ=2.50) for $^1$H NMR and dimethyl sulfoxide (δ=39.51) for $^{13}$C NMR. Data are reported as (br=broad, s=singlet, d=doublet, t=triplet, q=quartet, m=multiplet).

Abbreviations used in the following examples and elsewhere herein are:
atm atmosphere
br broad
DIPEA N,N-diisopropylethylamine
DMA N,N-dimethylacetamide
DMF N,N-dimethylformamide
ESI electrospray ionization
h hour(s)
HPLC high-performance liquid chromatography
LCMS liquid chromatography-mass spectrometry
m multiplet
MHz megahertz
min minutes
NMR nuclear magnetic resonance
ppm parts per million
TLC thin layer chromatography Example I-1: N-(5-((4-(1H-pyrrolo[2,3-b]pyridin-1-yl)pyrimidin-2-yl)amino)-2-((2-(dimethylamino)ethyl)(methyl)amino)-4-methoxyyphenyl)acrylamideN-(3-(1-(6-((2-methoxy-4-(4-methylpiperazin-1-yl)phenyl)amino)pyrimidin-4-yl)-3-phenyl ureido)phenyl)acrylamide

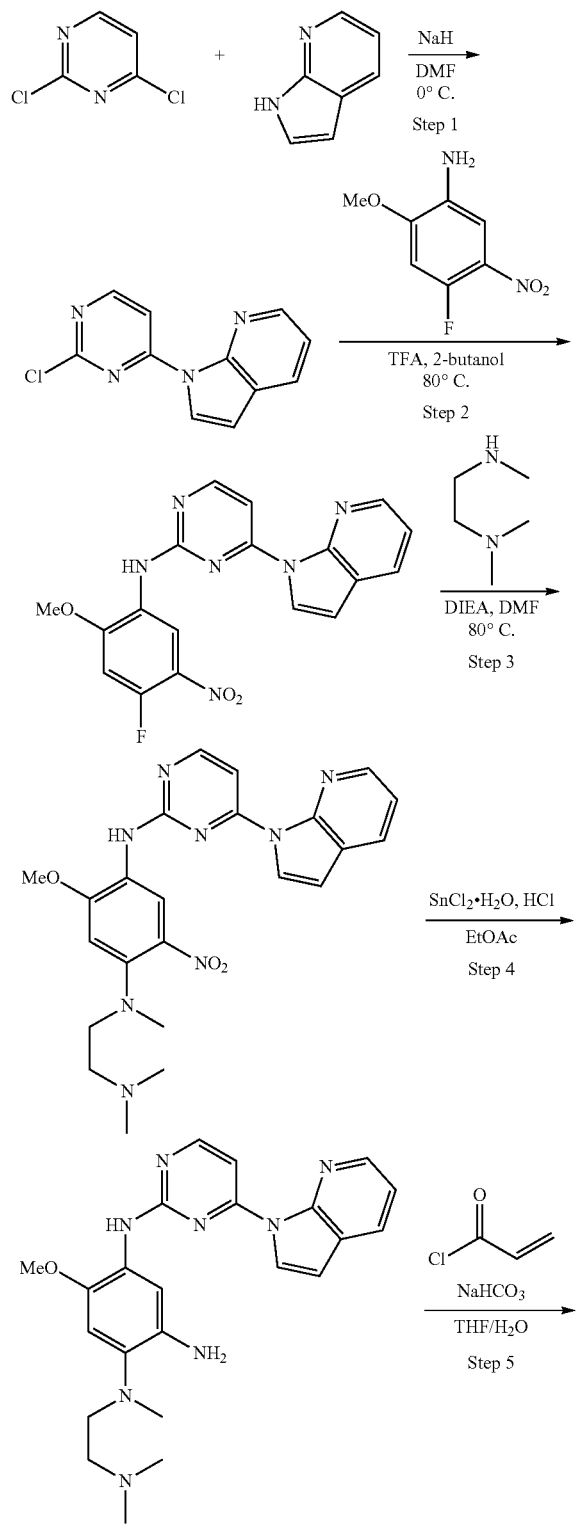

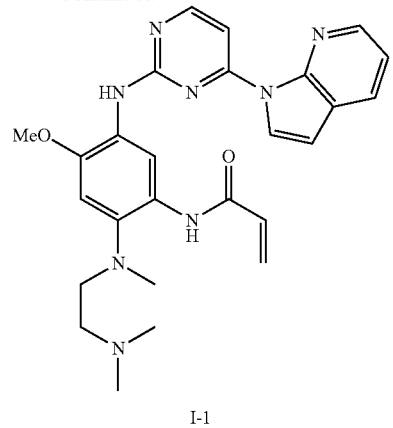 [SMILES: C=CC(=O)Nc1cc(Nc2nccc(-n3ccc4cccnc43)n2)c(OC)cc1N(C)CCN(C)C ; [I-]]

I-1

Step 1. 1-(2-chloropyrimidin-4-yl)-1H-indole

To a solution of 2,4-dichloropyrimidine (5 g) and 7-azaindole (3.6 g) in N,N-dimethylformamide (150 mL) was added sodium hydride portionwise at −20° C. After stirring for 30 min, the reaction mixture was quenched by water (700 mL) and the resulting precipitate was filtered off. The solid was blow-dried by nitrogen gas to obtain 1-(2-chloropyrimidin-4-yl)-1H-indole (4.77 g, 68%) as yellow solid.

Step 2. N-(4-fluoro-2-methoxy-5-nitrophenyl)-4-(1H-pyrrolo[2,3-b]pyridin-1-yl)pyrimidin-2-amine To a solution of 1-(2-chloropyrimidin-4-yl)-1H-indole (500 mg) and 4-fluoro-2-methoxy-5-nitroaniline (600 mg) in 2-butanol was added trifluoroacetic acid (0.25 mL). After stirred for 6 h at 80° C., the reaction mixture was diluted with dichloromethane and washed with saturated aqueous NaHCO$_3$. The organic layer was dried over Na$_2$SO$_4$, filtered and concentrated under reduced pressure. The resulting residue was purified by flash column chromatography on silica gel (1:99 to 60:40, EtOAc/CH$_2$Cl$_2$) to give N-(4-fluoro-2-methoxy-5-nitrophenyl)-4-(1H-pyrrolo[2,3-b]pyridin-1-yl)pyrimidin-2-amine (735 mg, 89%) as light yellow solid.

Step 3. N$^1$-(4-(1H-pyrrolo[2,3-b]pyridin-1-yl)pyrimidin-2-yl)-N$^4$-(2-(dimethylamino)ethyl)-2-methoxy-N$^4$-methyl-5-nitrobenzene-1,4-diamine To a solution of N-(4-fluoro-2-methoxy-5-nitrophenyl)-4-(1H-pyrrolo[2,3-b]pyridin-1-yl)pyrimidin-2-amine (300 mg) in N,N-dimethylformamide were added N$^1$,N$^1$,N$^2$-trimethylethane-1,2-diamine (0.15 mL) and DIEA (0.28 mL) and the resulting mixture was stirred at 80° C. After stirring for 6 h, the resulting solution was cooled to room temperature, diluted with dichloromethane and washed with saturated aqueous potassium carbonate solution and brine. The organic layer was dried over sodium sulfate, filtered and concentrated under reduced pressure. The resulting residue was purified by flash column chromatography (1:99 to 10:90, 1.75 N ammonia solution in MeOH/CH$_2$C$_{12}$) to obtain N$^1$-(4-(1H-pyrrolo[2,3-b]pyridin-1-yl)pyrimidin-2-yl)-N$^4$-(2-(dimethylamino)ethyl)-2-methoxy-N$^4$-methyl-5-nitrobenzene-1,4-diamine (310 mg, 85%) as off-white solid.

Step 4. N-(5-((4-(1H-pyrrolo[2,3-b]pyridin-1-yl)pyrimidin-2-yl)amino)-2-((2-(dimethyl amino)ethyl)(methyl)amino)-4-methoxyphenyl)acrylamide To a solution of N$^1$-(4-(1H-pyrrolo[2,3-b]pyridin-1-yl)pyrimidin-2-yl)-N$^4$-(2-(dimethylamino)ethyl)-2-methoxy- N⁴-methyl-5-nitrobenzene-1,4-diamine (150 mg) in ethyl acetate were added tin(II) chloride dehydrate (220 mg) and conc. HCl (0.1 mL). After stirring for 2 h at 50° C., the reaction mixture was diluted with ethyl acetate, neutralized with saturated NaHCO₃ and filtered. The filtrate was concentrated under reduced pressure and the resulting residue was used next step without further purification.

The crude N⁴-(4-(1H-pyrrolo[2,3-b]pyridin-1-yl)pyrimidin-2-yl)-N¹-(2-(dimethyl amino)ethyl)-5-methoxy-N¹-methylbenzene-1,2,4-triamine was dissolved in 1:1 mixture of tetrahydrofuran and saturated NaHCO₃. Acryloyl chloride (53 μL) was added to the reaction mixture and the resulting solution was stirred for 30 min. The resulting mixture was diluted with ethyl acetate, washed with water and brine, dried over Na₂SO₄, filtered and concentrated under reduced pressure. The resulting residue was purified by preparative high performance liquid chromatography (HPLC) to obtain N-(5-((4-(1H-pyrrolo[2,3-b]pyridin-1-yl)pyrimidin-2-yl)amino)-2-((2-(dimethylamino)ethyl)(methyl)amino)-4-methoxyphenyl)acrylamide (71 mg, 2 steps) as off-white solid. Rt=3.46 min, MS m/z: 487.36 [M+1], ¹H NMR 600 MHz (DMSO-d₆) δ 10.16 (s, 1H), 9.09 (s, 1H), 8.80 (d, J=3.6 Hz, 1H), 8.54 (d, J=5.4 Hz, 1H), 8.46 (d, J=5.4 Hz, 1H), 8.41 (dd, J=4.8, 1.8 Hz, 1H), 8.14 (s, 1H), 8.10 (dd, J=7.8, 1.8 Hz, 1H), 7.30 (dd, J=7.8, 4.8 Hz, 1H), 7.02 (s, 1H), 6.77 (d, J=4.2 Hz, 1H), 6.41 (dd, J=24.0, 10.2 Hz, 1H), 6.31 (dd, J=17.4, 2.4 Hz, 1H), 5.77 (dd, J=9.6, 1.8 Hz, 1H), 3.84 (s, 3H), 2.86 (t, J=6.0 Hz, 2H), 2.28 (bs, 2H), 2.19 (s, 6H).

The following compounds in Table 1 were synthesized according to the procedure outlined for Compound I-1 in Example 1.

TABLE 1

| Compound Number | Example | ¹H NMR and or MS (m/z) data |
| --- | --- | --- |
| I-2 | | Rt = 3.10 min, MS m/z: 486.36 [M + 1] |

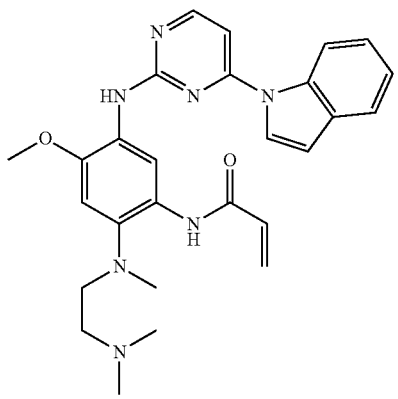 [SMILES: C=CC(=O)Nc1cc(Nc2nccc(-n3ccc4ccccc43)n2)c(OC)cc1N(C)CCN(C)C]

| I-3 | | Rt = 3.69 min, MS m/z: 486.36 [M + 1] |

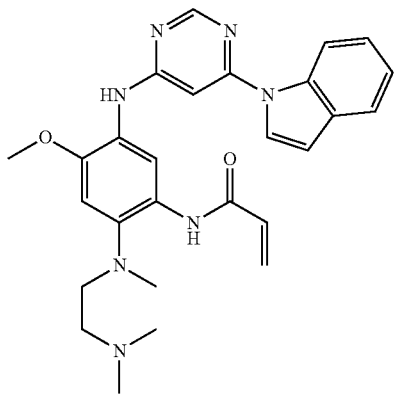 [SMILES: C=CC(=O)Nc1cc(Nc2cc(-n3ccc4ccccc43)ncn2)c(OC)cc1N(C)CCN(C)C]

TABLE 1-continued

| Compound Number | Example | ¹H NMR and or MS (m/z) data |
|---|---|---|
| I-4 | (structure) | Rt = 3.69 min, MS m/z: 500.38 [M + 1] |
| I-5 | (structure) | Rt = 3.55 min, MS m/z: 485.20 [M + 1] ¹H NMR 600 MHz (DMSO-d₆) δ 9.78 (s, 1H), 8.82 (s, 1H), 8.72 (s, 1H), 8.55 (d, J = 5.4 Hz, 1H), 8.47 (d, J = 6.0 Hz, 1H), 8.42 (dd, J = 4.8, 1.8 Hz, 1H), 8.21 (s, 1H), 8.11 (dd, J = 7.2, 0.6 Hz, 1H), 7.31 (dd, J = 7.8, 4.8 Hz, 1H), 6.88 (s, 1H), 6.77 (d, J = 3.6 Hz, 1H), 6.70 (dd, J = 16.8, 9.6 Hz, 1H), 6.34 (d, J = 16.8 Hz, 1H), 5.79 (d, J = 10.2 Hz 1H), 3.89 (s, 3H), 3.54 (m, 2H), 3.29 (m, 2H), 3.17 (d, J = 12.6 Hz, 2H) 3.02 (t, J = 12.0 Hz, 2H), 2.88 (s, 3H). |
| I-6 | (structure) | Rt = 3.50 min, MS m/z: 487.36 [M + 1] |
| I-7 | (structure) | Rt = 3.97 min, MS m/z: 520.31 [M + 1], ¹H NMR 600 MHz (DMSO-d₆) δ 9.44 (s, 1H), 8.92 (s, 1H), 8.62 (s, 1H), 8.12 (s, 1H), 7.83 (d, J = 3.0 Hz, 1H), 7.74 (d, J = 7.8 Hz, 1H), 7.59 (d, J = 7.8 Hz, 1H), 7.16-7.11 (m, 2H), 6.97 (s,1H), 6.73 (d, J = 3.6 Hz, 1H), 6.62-6.56 (m, 1H), 6.28 (d, J = 16.8 Hz, 1H), 5.77 (d, J = 10.8 Hz 1H), 3.83 (s, 3H), 3.29-3.20 (m, 4H), 2.76 (s, 3H), 2.76 (s, 3H), 2.57 (s, 3H). |

TABLE 1-continued
| Compound Number | Example | ¹H NMR and or MS (m/z) data |
|---|---|---|
| I-8 | 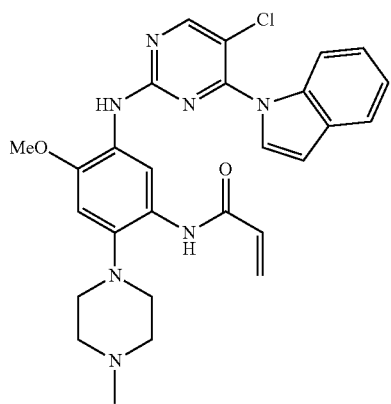 | Rt = 3.98 min, MS m/z: 518.30 [M + 1], ¹H NMR 600 MHz (DMSO-d$_6$) δ 8.93 (s, 2H), 8.59 (s, 1H), 8.07 (s, 1H), 7.82 (d, J = 3.6 Hz, 1H), 7.74-7.70 (m, 1H), 7.60-7.56 (m, 1H), 7.16-7.12 (m, 2H), 6.83 (s, 1H), 6.71 (d, J = 3.6 Hz, 1H), 6.62-6.56 (m, 1H), 6.19 (d, J = 16.8 Hz, 1H), 5.71 (d, J = 10.8 Hz, 1H), 3.79 (s, 3H), 2.86-2.82 (m, 4H), 2.54-2.48 (m, 4H), 2.23 (s, 3H). |
| I-9 | 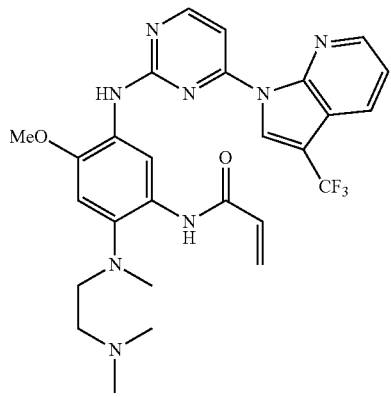 | Rt = 4.06 min, MS m/z: 555.35 [M + 1] |
| I-10 | 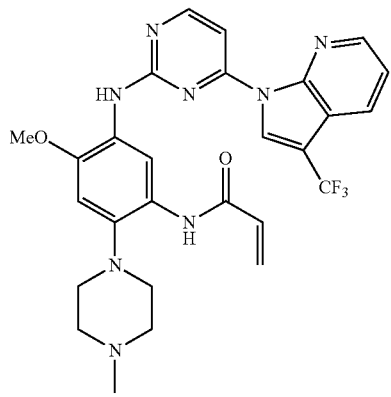 [SMILES: C=CC(=O)Nc1cc(Nc2nccc(-n3cc(C(F)(F)F)c4cccnc43)n2)c(OC)cc1N1CCN(C)CC1] | Rt = 4.06 min, MS m/z: 553.30 [M + 1] |

TABLE 1-continued

| Compound Number | Example | ¹H NMR and or MS (m/z) data |
|---|---|---|
| I-11 | | Rt = 3.49 min, MS m/z: 485.20 [M + 1] ¹H NMR 600 MHz (DMSO-$d_6$) δ 9.78 (s, 1H), 8.82 (s, 1H), 8.72 (s, 1H), 8.55 (d, J = 5.4 Hz, 1H), 8.47 (d, J = 6.0 Hz, 1H), 8.42 (dd, J = 4.8, 1.8 Hz, 1H), 8.21 (s, 1H), 8.11 (dd, J = 7.2, 0.6 Hz, 1H), 7.31 (dd, J = 7.8, 4.8 Hz, 1H), 6.88 (s, 1H), 6.77 (d, J = 3.6 Hz, 1H), 6.70 (dd, J = 16.8, 9.6 Hz, 1H), 6.34 (d, J = 16.8 Hz, 1H), 5.79 (d, J = 10.2 Hz 1H), 3.89 (s, 3H), 3.54 (m, 2H), 3.29 (m, 2H), 3.17 (d, J = 12.6 Hz, 2H) 3.02 (t, J = 12.0 Hz, 2H), 2.88 (s, 3H). |
| I-12 | | Rt = 3.41 min, MS m/z: 502.36 [M + 1], ¹H NMR 600 MHz (DMSO-$d_6$) δ 9.49 (s, 1H), 9.32 (s, 1H), 8.68 (bs, 1H), 8.26 (s, 1H), 7.59-7.54 (m, 1H), 7.27 (bs, 1H), 7.20-7.12 (m, 2H), 7.09 (bs, 1H), 6.99 (s, 1H), 6.67 (d, J = 3.0 Hz, 1H), 6.68-6.60 (m, 1H), 6.31 (d, J = 17.4 Hz, 1H), 5.79 (d, J = 17.4 Hz, 1H), 3.84 (s, 3H), 3.32-3.24 (m, 4H), 2.80 (s, 3H), 2.80 (s, 3H), 2.62 (s, 3H). |
| I-13 | | Rt = 3.44 min, MS m/z: 500.38 [M + 1], ¹H NMR 600 MHz (DMSO-$d_6$) δ 9.77 (s, 1H), 9.04 (s, 1H), 8.65 (bs, 1H), 8.40 (bs, 1H), 8.28 (s, 1H), 7.60-7.54 (m, 1H), 7.25 (bs, 1H), 7.20-7.10 (m, 2H), 7.08 (bs, 1H), 6.86 (s, 1H), 6.70-6.65 (m, 1H), 6.66 (d, J = 3.6 Hz, 1H), 6.25 (d, J = 17.4 Hz 1H), 5.75 (d, J = 10.8 Hz, 1H), 3.82 (s, 3H), 3.54 (d, J = 12.0 Hz, 2H), 3.32-3.24 (m, 2H), 3.19 (d, J = 12.6 Hz, 2H) 3.02 (t, J = 11.4 Hz, 2H), 2.88 (d, J = 3.0 Hz, 3H). |

TABLE 1-continued

| Compound Number | Example | $^1$H NMR and or MS (m/z) data |
|---|---|---|
| I-14 | | Rt = 3.70 min, MS m/z: 501.40 [M + 1] |
| I-15 | | Rt = 2.69 min, MS m/z : 487.44 [M + 1] $^1$H NMR 600 MHz (DMSO-d$_6$) δ 9.57 (s, 1H), 9.22 (s, 1H), 8.45 (s, 1H), 8.38 (d, J = 3.6 Hz, 1H), 8.37 (d, J = 1.8 Hz, 1H), 8.16 (s, 1H), 8.11 (dd, J = 7.8, 1.2 Hz, 1H), 7.29 (dd, J = 7.2, 4.2 Hz, 1H), 6.99 (s, 1H), 6.61 (dd, J = 16.8, 9.6 Hz, 1H), 6.29 (dd, J = 16.8, 1.8 Hz, 1H), 5.78 (d, J = 16.2 Hz, 1H), 3.85 (s, 3H), 3.26 (t, J = 6.0 Hz, 2H), 3.10 (t, J = 5.4 Hz, 2H), 2.80 (s, 3H), 2.79 (s, 3H), 2.61 (s, 3H). |

Example 2: Biochemical Studies

Kinase Inhibitors

WZ4002, AZD9291 and CO-1686 were synthesized using previously published methods (Zhou, W., et al., Nature 462, 2009, 1070-4; Walter, A. O., et al., Cancer Discov. 3, 2013, 1404-15; Cross, D. A., et al., Cancer Discov. 2014). Gefitinib, Afatinib, Neratinib, and CL-387,785 were obtained from Selleck chemicals. Stock solutions of all drugs were prepared in DMSO and stored at −80° C.

Cell Culture and Reagents

The EGFR mutant NSCLC cell lines HCC827 (del E746_A750), H3255 (L858R), H3255GR (L858R/T790M), H3255DR (L858R/T790M Amplified), HCC827EPR (del E746_A750/T790M), H1975 (L858R/T790M) PC9 (del E746_A750), PC9 GR (del E746_A750/T790M), PC9 DR (del E746_A750/T790M amplified) and SNU2315 (del E746_A750/T790M), were obtained from Dr. Adi Gazdar (UT Southwestern, Dallas, Tex.), American Type Culture Collection, or from the Korean Cell Line Bank (Seoul National University, Seoul, Korea) and have been previously characterized (Zhou, W. et al., Nature. 2009; 462:1070-4; Ercan, D., et al., Oncogene. 29, 2010, 2346-56; Suda, K., et al., Clin Cancer Res. 16, 2010, 5489-98; Ku, J. L., et al., Cell Oncol (Dordr). 34, 2011, 45-54).

All cell lines were authenticated in September 2014 using the Promega Geneprint 16 cell ID system and were performed at the Research Technology Support Facility at Michigan State University. All cell lines were maintained in RPMI 1640 (Invitrogen, Carlsbad, Calif.) supplemented with 10% FBS 100 units/mL penicillin, 100 units/mL streptomycin, and 2 mM glutamine. H3255, H3255GR and H3255DR were maintained in ACL-4 media (Invitrogen, Carlsbad, Calif.) supplemented with 5% FBS, 100 units/mL penicillin, 100 units/mL streptomycin, and 2 mM glutamine. The EGFR mutant Ba/F3 cells and the NIH-3T3 cells have been previously characterized (Zhou, W. et al., Nature. 462, 2009, 1070-4).

Generation of Drug-Resistant Cells Lines

The EGFR L718Q and L844V mutations were introduced via site directed mutagenesis using the Quick Change Site-Directed Mutagenesis kit (Stratagene; La Jolla, Calif.) according to the manufacturer's instructions. The L718Q mutation was generated using forward primer 5'-aaaaagat-caaagtgcagggctccggtgcgttc-3' (SEQ. ID. NO. 1) and reverse primer 5' gaacgcaccggagccctgcactttgatcttttt-3' (SEQ. ID. NO. 2). The L844V mutation was generated using forward primer 5'-cctggcagccaggaacgtagtggtgaaaaca-3' (SEQ. ID. NO. 3) and reverse primer 5'-tgttttcaccac-tacgttcctggctgccagg-3' (SEQ. ID. NO. 4). All constructs were confirmed by DNA sequencing. The constructs were shuttled into the retroviral vector JP1540 or lentiviral vector JP1698 using the BD Creator System (BD Biosciences). Ba/F3, NIH-3T3, cells were infected with retrovirus and PC9GR4 and HCC827 EPR cells infected with lentivirus according to standard protocols, as described previously (Engelman, J. A., et al., Proc Natl Acad Sci USA. 2005; 102:3788-93). Stable clones were obtained by selection in puromycin (2 μg/ml).

Cell Proliferation Assays and Growth Assays

Growth and inhibition of growth was assessed by MTS assay and was performed according to previously established methods (Zhou, W., et al., Nature. 462, 2009, 1070-4; Ercan, D., et al., Cancer Discov. 934, 2012, 934-47). NSCLC or Ba/F3 cells were exposed to treatment for 72 hours and the number of cells used per experiment determined empirically and has been previously established (Zhou, W., et al., Nature. 462, 2009, 1070-4; Ercan, D., et al., Cancer Discov. 2, 2012, 934-47). All experimental points were set up in six wells and all experiments were repeated at least three times. The data was graphically displayed using GraphPad Prism version 5.0 for Windows, (GraphPad Software; www.graphpad.com). The curves were fitted using a non-linear regression model with a sigmoidal dose response.

For clonogenic assays, 1000 cells were seeded in a 6 well plate and allowed to adhere overnight then treated with 400 nM of indicated drug. After 7 days, wells were fixed with 0.5% Crystal Violet solution. Number of colonies was quantified using Adobe Photoshop version CS4 Extended analysis tool. All experimental points were set up in three wells and all experiments were repeated at least twice. Data were graphically displayed using GraphPad Prism version 5.0 for Windows Table 2 shows the cell proliferation data of the mutant EGFR inhibitors WZ4002, AZD9291, and Compound I-1 in various mutant EGFR cell lines.

chemiluminescence system (Perkin Elmer Inc.). Anti-phospho-Akt (Ser-473), anti-total Akt antibodies are obtained from Cell Signaling Technology. The phospho-specific EGFR (pY1068), total ERK1/2, phospho-ERK1/2 (pT185/pY187) antibodies are purchased from Invitrogen. Total EGFR antibody is purchased from Bethyl Laboratories. Tubulin antibody is purchased from Sigma.

Immunoprecipitation Using Biotinylated WZ4002 (TX2-30)

For the synthesis of TX2-30, the warhead part of WZ4002 was synthesized as previously shown (Nature 2009). The biotin tail was introduced following the procedure from ZW, H W et al Chem. Biol. 2010. Briefly, cell lysate was incubated with indicated concentrations of TX2-30 for 1 hour at 4 C. Excess compound was removed using DG-10 column (Bio-Rad, Hercules, Calif.). The protein was further denatured with 8M Urea solution. The addition of Streptavidin beads (Sigma) was followed by 1 hour incubation at room temperature. Beads were washed 3 times and biotin labeled EGFR was released by heating beads to 95° C. in SDS buffer.

Chemical Cross-Linking of EGFR Ba/F3 Intact Cells

Cells were treated with Cetuximab (10 μg/ml) for 16 hours. Following treatment, cells were washed twice with cold PBS and incubated with 1.0 Mm bis(sulfosuccinimidy) suberate (Thermo Scientific, Rockfrod, Ill.) for 30 minutes at room temperature. The reactions were quenched with the addition of 20 mM Tris, (pH7.4). Cells were then washed twice with PBS and then lysed with NP40 buffer.

TABLE 2

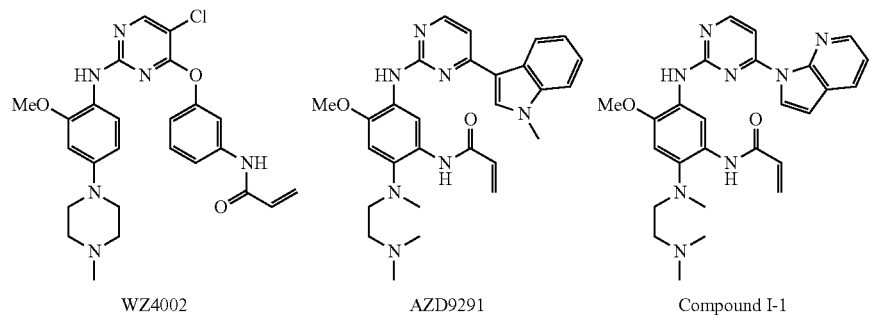 [SMILES: C=CC(=O)Nc1cccc(Oc2nc(Nc3ccc(N4CCN(C)CC4)cc3OC)ncc2Cl)c1 ; C=CC(=O)Nc1cc(Nc2nccc(-c3cn(C)c4ccccc34)n2)c(OC)cc1N(C)CCN(C)C ; C=CC(=O)Nc1cc(Nc2nccc(-n3ccc4cccnc43)n2)c(OC)cc1N(C)CCN(C)C]

| Ba/F3 Oncogene | Mutation | WZ4002 $IC_{50}$ = nM | AZD9291 $IC_{50}$ = nM | Compound I-1 $IC_{50}$ = nM |
|---|---|---|---|---|
| EGFR | WT | 100 | 23.01 | 323 |
| EGFR | L718Q | 2891 | 1247.5 | NT |
| EGFR | L844V | 2849 | 284.5 | NT |
| EGFR | DEL | 8.4 | 1.79 | 42.85 |
| EGFR | DEL/L718Q | 1492.0 | 55.37 | 176 |
| EGFR | DEL/844V | 956.5 | 15.09 | 53.09 |
| EGFR | DEL/T790M | 19.2 | 10.04 | 64.75 |
| EGFR | DEL/T790M/L718Q | 2005.5 | 576 | 644 |
| EGFR | DEL/T790M/L844V | 822.5 | 21.6 | 89 |
| EGFR | L858R | 6.8 | 1.98 | 60 |
| EGFR | L858R/L718Q | 2744.5 | 1179.5 | 2055 |
| EGFR | L858R/L844V | 860.5 | 29.215 | 283 |
| EGFR | L858R/T790M | 14.2 | 10 | 189 |
| EGFR | L858R/T790M/L718Q | 2227.5 | 1272.5 | 1972 |

Antibodies and Western Blotting

Cells grown under the previously specified conditions were lysed in NP-40 buffer (Cell Signaling Technology). Western blot analyses are conducted after separation by SDS/PAGE electrophoresis and transfer to polyvinylidene difluoride-P membrane (Millipore). Immunoblotting is performed according to the antibody manufacturers' recommendations. Antibody binding is detected using an enhanced Pepsin Digestion and Peptide Analysis For the elucidation of the modification site, all three proteins (50 pmol each) were digested offline with pepsin in an enzyme:substrate ratio of 1:1. The pepsin digestion was performed in a potassium phosphate buffer (75 mM $KH_2PO_4$/75 mM $K_2HPO_4$) pH 2.5. The reaction was carried out for 5 minutes on ice. The resulting peptides were injected into a Waters nanoAcquity UPLC system (Waters, Milford, Mass.) and trapped and desalted for 3 min at 100 μL/min and then separated in 60 min by an 8%-40% acetonitrile:water gradient at 40 μL/min. The separation column was a 1.0× 100.0 mm ACQUITY UPLC C18 BEH (Waters) containing 1.7 μm particles.

Mass spectra were obtained with a Waters QTOF Premier equipped with standard ESI source (Waters Corp., Milford, Mass., USA). The instrument configuration was the following: capillary was 3.5 kV, trap collision energy at V, sampling cone at 37 V, source temperature of 100° C. and desolvation temperature of 250° C. Mass spectra were acquired over an m/z range of 100 to 2000. Mass accuracy was ensured by calibration with 100 fmol/μL GFP, and was less than 10 ppm throughout all experiments. Identification of the peptic fragments was accomplished through a combination of exact mass analysis and $MS^{E12}$ using custom Identity Software from the Waters Corporation. $MS^E$ was performed by a series of low-high collision energies ramping from 5-25 V, therefore ensuring proper fragmentation of all the peptic peptides eluting from the LC system.

Generation of Mouse Cohorts and Treatment with Compounds of Formula (I)

EGFR-TL (T790M/L858R) mice are generated as previously described (Li, D. et al. Cancer Cell 12, 81-93 (2007)). EGFR exon 19 Deletion-T790M (TD) inducible bitransgenic mice are similarly generated and characterized. Briefly, exon 19 deletion is introduced in the human EGFR gene through site directed mutagenesis in the pTRE2-hyg-EGFR-T790M. The constructs were then digested with XhoI to release the entire allele containing Tet-op-EGFR TD-beta-globin PolyA. Transgenic mice are then generated by injection of the construct into FVB/N fertilized eggs. Progeny are genotyped through PCR exactly the same as reported. Founders are crossed with CCSP-rtTA mice and inducible bitransgenic mice with high and inducible expression of the mutant hEGFR transgene are identified and expanded for subsequent analyses and experiments. All mice are housed in a pathogen-free environment at the Harvard School of Public Health and are handled in strict accordance with Good Animal Practice as defined by the Office of Laboratory Animal Welfare, and all animal work is done with Dana-Farber Cancer Institute IACUC approval.

Cohorts of EGFR TL/CCSP-rtTA and EGFR TD/CCSP-rtTA are put on doxycycline diet at 5 weeks of age to induce the expression of mutant EGFR. These mice undergo MRI after 6 to 8 weeks of doxycycline diet to document and quantify the lung cancer burden before being assigned to various treatment study cohorts. There is a minimum of 3 mice per treatment group. Mice are then treated either with vehicle (NMP (10% 1-methyl-2-pyrrolidinone: 90% PEG-300) alone or a compound of Formula (I) at 25 mg/kg gavage daily. After 2 weeks of treatment, these mice undergo a second round of MRI to document their response to the treatment. MRIs and tumor burden measurement were performed as described previously (Li, D. et al. Cancer Cell 12, 81-93 (2007); Ji, H. et al. Cancer Cell 9, 485-95 (2006)).

MRI Scanning and Tumor Volume Measurement

Mice are anesthetized with 1% isoflurane in an oxygen/air mixture. The respiratory and cardiac rates of anesthetized mice are monitored using Biotrig Software. The animals are imaged with a rapid acquisition with relaxation enhancement (RARE) sequence (TR=2000 ms, TE effect=25 ms) in the coronal and axial planes with a 1 mm slice thickness and with sufficient number of slices to cover the entire lung. Matrix size of 128×128 and a field of view (FOV) of 2.5 cm×2.5 cm² are used for all imaging. With same geometry and described above, the mice are also imaged with a gradient echo fast imaging (GEFI) sequence (TR=180 ms, TE effect=2.2 ms) with respiratory and cardiac gating, in both coronal and axial planes. The detailed procedure for MRI scanning has been previously described (Li, D. et al!.. Cancer Cell 12, 81-93 (2007); Ji, H. et al. Cancer Cell 9, 485-95 (2006)).

Immunohistochemical Analyses

Hematoxylin and eosin (H&E) staining of tumor sections is performed at the Department of Pathology at the Brigham and Women's Hospital. Immunohistochemistry is performed on formal fixed paraffin embedded tumor sections. The antibodies used are: total EGFR and phospho-EGFR Y1068 (Cell Signaling Technology) and Ki67. Apoptosis is measured by counting nuclear bodies in H&E stained sections and by a terminal deoxynucleotidyl-transferase mediated dUTP-biotin nick end labeling (TUNEL) assay.

Pharmacokinetic Analyses

Dose administration: All mice are weighed before dose administration and randomized. For intravenous administration, a freshly prepared solution of a compound of Formula (I) is administered at a dose level of 1 mg/kg via tail vein at a slow and steady rate. The dosing volume for intravenous administration is 5 mL/kg. Freshly prepared suspension of a compound of Formula (I) is administered at an oral dose of 10 mg/kg, by stomach intubation using a 16 gauge oral feeding needle. The dosing volume for oral dose group is 10 mL/kg.

Blood samples: Blood samples (0.06 mL) are collected from saphenous vein of each mouse at regular intervals. During each sampling point, blood samples are collected in labeled microtubes containing K2EDTA as an anticoagulant. Samples are centrifuged at 4000 rpm for 10 min at 4±2° C. (Centrifuge Model: Kubota 3500). The recovered quantity of plasma from each sample is transferred to labeled microtubes. The plasma samples are stored at −70° C. until bioanalysis.

Bioanalysis of samples: Bioanalytical method for the determination of a compound of Formula (I) in mouse plasma is developed using LC-MS/MS equipment. The method is partially validated prior to sample analysis.

Pharmacokinetic analysis: The pharmacokinetic parameters of a compound of Formula (I) such as $T_{max}$, $C_{max}$, AUC, CL, $V_d$, $T_{1/2}$, and bioavailability in mouse plasma are determined from the concentration-time data using non-compartmental analysis (WinNonlin Enterprise version 5.2, Pharsight Corporation, USA).

Serum Creatinine and White Blood Cell Count Analyses

Blood is collected from vehicle and compound of Formula (I) treated mice into appropriate tubes and analyzed at the clinical laboratory at the Boston Children's Hospital.

Statistical Analyses

Statistical analyses were performed using an unpaired two tailed Student's t-test. A p value of less than 0.05 was considered significant.

The selectivity between wild-type EGFR and the L858R/T790M, Exon 19 Deletion/T790M, Del/T790M/L718Q, or L858R/T790M/L718Q EGFR mutants is measured using cellular proliferation assays where cell proliferation is completely dependent on kinase activity. For example, murine Ba/F3 cells transfected with a suitable version of wild-type EGFR (containing a WT EGFR kinase domain), or Ba/F3 cells transfected with L858R/T790M, Exon 19 Deletion/T790M, Del/T790M/L718Q, or L858R/T790M/L718Q are used. Proliferation assays were performed at a range of inhibitor concentrations (10 μM, 3 μM, 1.1 μM, 330 nM, 110 nM, 33 nM, 11 nM, 3 nM, 1 nM) and an $EC_{50}$ is calculated.

An alternative method to measure effects on EGFR activity is to assay EGFR phosphorylation. Wild type or mutant (L858R/T790M, Del/T790M, Del/T790M/L718Q, or L858R/T790M/L718Q) EGFR was transfected into NIH-3T3 cells (which do not normally express endogenous EGFR) and the ability of the inhibitor (using concentrations as above) to inhibit EGFR phosphorylation was assayed. Cells were exposed to increasing concentrations of inhibitor for 6 hours and stimulated with EGF for 10 minutes. The effects on EGFR phosphorylation were assayed by Western Blotting using phospho-specific (Y1068) EGFR antibodies.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A method of treating non-small cell lung cancer comprising administering to a subject in need thereof an effective amount of a compound of Formula I:

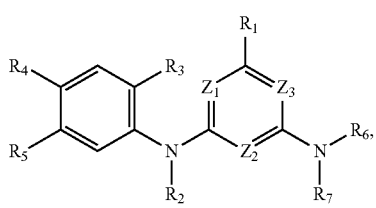

or pharmaceutically acceptable salts, hydrates, solvates, stereoisomers, or tautomers thereof, wherein:
$Z_1$ and $Z_2$ are each independently N and $Z_3$ is $CR_8$;
$R_8$ is H, $(C_1-C_4)$ alkyl, $(C_1-C_4)$ haloalkyl, or halogen;
$R_1$ is H, $(C_1-C_4)$ alkyl, $(C_1-C_4)$ haloalkyl, $NH_2$, $NH(C_1-C_4)$ alkyl, $N((C_1-C_4)$ alkyl$)_2$, or halogen;
$R_2$ is H or $(C_1-C_6)$ alkyl;
$R_3$ is $(C_1-C_4)$ alkoxy, $(C_1-C_4)$ alkyl, $(C_1-C_4)$ haloalkyl, or halogen;
$R_4$ is $NR_9R_{10}$ or a 5- to 7-membered heterocycle comprising 1-3 heteroatoms selected from N, O, and S and optionally substituted with one or more $R_{11}$;
$R_9$ is H or $(C_1-C_4)$ alkyl;
$R_{10}$ is $(C_1-C_4)$ alkyl, $(C_1-C_4)$ alkyl-$NH(C_1-C_4)$ alkyl, or $(C_1-C_4)$ alkyl-$N((C_1-C_4)$ alkyl$)_2$;
or $R_9$ and $R_{10}$ together with the nitrogen atom to which they are attached form a 5- to 7-membered heterocycle optionally comprising 1 or 2 additional heteroatoms selected from N, O, and S and optionally substituted with one or more $R_{11}$;
each $R_{11}$ is independently $(C_1-C_4)$ alkyl, $(C_1-C_4)$ haloalkyl, $(C_1-C_4)$ alkoxy, or halogen;
$R_5$ is $NR_{12}C(O)R_{13}$ or $C(O)NR_{12}R_{13}$;
$R_{12}$ is H or $(C_1-C_6)$ alkyl;
$R_{13}$ is $(C_1-C_5)$ alkyl or $(C_2-C_6)$ alkenyl, wherein the alkyl or alkenyl is optionally substituted with one or more substituents independently selected from halogen, OH, CN, and $NH_2$;
$R_6$ and $R_7$ together with the nitrogen atom to which they are attached form a substituent of the formula

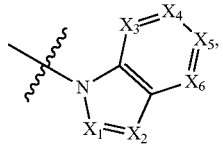

wherein
$X_3$ is N;
$X_1$, $X_2$, $X_4$, $X_5$ and $X_6$ are each independently CH; and
each $R_{15}$ is independently $(C_1-C_6)$ alkyl, $(C_1-C_6)$ haloalkyl, $(C_1-C_6)$ alkoxy, OH, $NH_2$, $NH(C_1-C_6)$ alkyl, $N((C_1-C_6)$ alkyl$)_2$, or halogen.

2. The method of claim 1, wherein $R_1$ is H or $NH_2$.
3. The method of claim 1, wherein $R_2$ is H.
4. The method of claim 1, wherein $R_3$ is $(C_1-C_4)$ alkoxy.
5. The method of claim 1, wherein $R_4$ is $NR_9R_{10}$.
6. The method of claim 1, wherein $R_5$ is $NR_{12}C(O)R_{13}$.
7. The method of claim 1, wherein $R_{15}$ is selected from $(C_1-C_6)$ alkyl and $(C_1-C_6)$ haloalkyl.
8. The method of claim 1, wherein $R_8$ is H or halogen.
9. The method of claim 1, wherein $R_9$ is $(C_1-C_4)$ alkyl.
10. The method of claim 1, wherein $R_{10}$ is $(C_1-C_4)$ alkyl-$NH(C_1-C_4)$ alkyl, or $(C_1-C_4)$ alkyl-$N((C_1-C_4)$ alkyl$)_2$.
11. The method of claim 1, wherein $R_4$ is $NR_9R_{10}$ and $R_9$ and $R_{10}$ together with the nitrogen atom to which they are attached form a 5- to 7-membered heterocycle optionally comprising 1 or 2 additional heteroatoms selected from N, O, and S-and optionally substituted with one or more $R_{11}$.
12. The method of claim 1, wherein $R_{11}$ is $(C_1-C_4)$ alkyl, $R_{12}$ is H, and $R_{13}$ is $(C_2-C_6)$ alkenyl.
13. The method of claim 1, wherein $R_{11}$ is $(C_1-C_4)$ alkyl, $R_{12}$ is $(C_1-C_6)$ alkyl, and $R_{13}$ is $(C_2-C_6)$ alkenyl.
14. The method of claim 1, wherein at least one of $X_1$, $X_2$, $X_4$, $X_5$ and $X_6$ is $CR_{15}$.
15. The method of claim 1, wherein $R_{15}$ is selected from methyl and $CF_3$.
16. The method of claim 1, wherein the compound is of Formula (Ia):

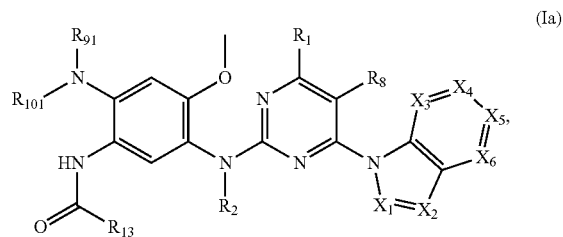

or pharmaceutically acceptable salts, hydrates, solvates, stereoisomers, or tautomers thereof, wherein:
$X_1$, $X_2$, $X_4$, $X_5$ and $X_6$ are each independently CH or $CR_{15}$;
$R_{91}$ is $(C_1-C_4)$ alkyl;
$R_{101}$ is $(C_1-C_4)$ alkyl-$NH(C_1-C_4)$ alkyl or $(C_1-C_4)$ alkyl-$N((C_1-C_4)$ alkyl$)_2$;
or $R_{91}$ and $R_{101}$ together with the nitrogen atom to which they are attached form a 5- to 7-membered heterocycle optionally comprising 1 or 2 additional heteroatoms selected from N, O, and S and optionally substituted with one or more $R_{11}$;
each $R_{11}$ is independently $(C_1-C_4)$ alkyl, $(C_1-C_4)$ haloalkyl, $(C_1-C_4)$ alkoxy, or halogen; and $R_{13}$ is $(C_1-C_6)$ alkyl or $(C_2-C_6)$ alkenyl, wherein the alkyl or alkenyl is optionally substituted with one or more substituents independently selected from halogen, OH, CN, and $NH_2$.

17. The method of claim 1, wherein the compound is selected from the group consisting of:

N-(5-((4-(1H-pyrrolo[2,3-b]pyridin-1-yl)pyrimidin-2-yl) amino)-2-((2-(dimethylamino)ethyl) (methyl)amino)-4-methoxyphenyl)acrylamide;

N-(2-((2-(dimethylamino)ethyl)(methyl)amino)-4-methoxy-5-((4-(3-(trifluoromethyl)-1H-pyrrolo[2,3-b] pyridin-1-yl)pyrimidin-2-yl)amino)phenyl)acrylamide;

N-(4-methoxy-2-(4-methylpiperazin-1-yl)-5-((4-(3-(trifluoromethyl)-1H-pyrrolo[2,3-b]pyridin-1-yl)pyrimidin-2-yl)amino)phenyl)acrylamide;

N-(5-((4-(1H-pyrrolo[2,3-b]pyridin-1-yl)pyrimidin-2-yl) amino)-4-methoxy-2-(4-methylpiperazin-1-yl)phenyl) acrylamide; and N-(2-((2-(dimethylamino)ethyl)(methyl)amino)-4-methoxy-5-((4-(3-methyl-1H-pyrrolo[2,3-b]pyridin-1-yl)pyrimidin-2-yl)amino)phenyl)acrylamide.

18. The method of claim 1, wherein the non-small cell lung cancer is characterized by a mutation in EGFR selected from the group consisting of T790M, L718Q, L844V, L858R, Del, Del/L718Q, Del/L844V, Del/T790M, L858R/T790M, Del/T790M/L718Q, Del/T790M/L844V, L858R/L844V, L858R/L718Q, L858R/T790M/L718Q, and exon 19 deletion/T790M.

\* \* \* \* \*